United States Patent [19]

Dower et al.

[11] Patent Number: 5,639,603
[45] Date of Patent: Jun. 17, 1997

[54] SYNTHESIZING AND SCREENING MOLECULAR DIVERSITY

[75] Inventors: William J. Dower, Menlo Park; Ronald W. Barrett, Sunnyvale; Mark A. Gallop, Palo Alto; Michael C. Needels, Oakland, all of Calif.

[73] Assignee: Affymax Technologies N.V., Curacao, Netherlands Antilles

[21] Appl. No.: 146,886

[22] Filed: Nov. 2, 1993

Related U.S. Application Data

[63] Continuation-in-part of Ser. No. 946,239, Sep. 16, 1992, which is a continuation-in-part of Ser. No. 762,522, Sep. 18, 1991, abandoned.

[51] Int. Cl.$^6$ .................................................. C12Q 1/68
[52] U.S. Cl. ........................ 435/6; 530/334; 530/335; 536/25.3
[58] Field of Search .................... 536/25.3; 530/334, 530/335; 435/6

[56] References Cited

U.S. PATENT DOCUMENTS

| | | | |
|---|---|---|---|
| 4,182,654 | 1/1980 | Royer | 435/272 |
| 4,315,074 | 2/1982 | Royer | 435/70 |
| 4,587,044 | 5/1986 | Miller et al. | 530/211 |
| 4,631,211 | 12/1986 | Houghton | 428/35 |
| 4,671,941 | 6/1987 | Niina et al. | 422/131 |
| 4,701,304 | 10/1987 | Horn et al. | 422/62 |
| 4,713,326 | 12/1987 | Dattagupta | 435/6 |
| 4,755,558 | 7/1988 | Kalbag | 525/54.1 |
| 4,794,150 | 12/1988 | Steel | 525/54.11 |
| 4,818,681 | 4/1989 | Dattagupta | 435/6 |
| 4,833,092 | 5/1989 | Geysen | 436/501 |
| 4,855,225 | 8/1989 | Fung et al. | 435/6 |
| 4,882,269 | 11/1989 | Schneider et al. | 435/6 |
| 4,965,188 | 10/1990 | Mullis et al. | 435/6 |
| 5,010,175 | 4/1991 | Rutter et al. | 530/334 |
| 5,143,854 | 9/1992 | Pirrung | 436/518 |
| 5,264,563 | 11/1993 | Huse | 536/25.3 |
| 5,324,483 | 6/1994 | Cody et al. | 422/131 |

FOREIGN PATENT DOCUMENTS

| | | | |
|---|---|---|---|
| 0392546 | 12/1990 | European Pat. Off. | C12Q 1/68 |
| 392546 | 12/1990 | European Pat. Off. | C12Q 1/68 |
| 90/00626 | 1/1990 | WIPO . | |
| 90/14441 | 11/1990 | WIPO | C12Q 1/68 |
| 90/15070 | 12/1990 | WIPO | C07K 1/04 |
| 92/00091 | 1/1992 | WIPO | A61K 37/02 |
| 92/03461 | 3/1992 | WIPO | C07H 7/00 |
| 92/06176 | 4/1992 | WIPO | C12N 1/24 |
| 92/10092 | 6/1992 | WIPO | A01N 1/02 |
| 93/20242 | 10/1993 | WIPO | C12Q 1/70 |
| 94/02515 | 2/1994 | WIPO | C07K 7/06 |
| 94/08051 | 4/1994 | WIPO | C12Q 1/68 |

OTHER PUBLICATIONS

*Advances in Analytical Chemistry and Instrumentation*, Charles N. Reilley, Ed., John Wiley & Sons, Inc., 1964, pp. 56–59.

Frank et al., "Simultaneous Multiple Peptide Synthesis Under Continuous Flow Conditions on Cellulose Paper Discs as Segmental Solid Supports," *Tetrahedron Letters* (1988) 44:6031–6040.

Arnold et al., "Room–Temperature Microparticle–Based Persistent Spectral Hole Burning Memory," *Optics Letters* 16(6):420–422 (1991).

Baldwin et al., "New Photolabile Phosphate Protecting Groups," *Tetrahedron* 46(190:6879–6884 (1990).

Barr et al., "7–Deaza–2'–Deoxyguanosine–5'–Triphosphate: Enhanced Resolution in M13 Dideoxy Sequencing," *Bio. Techniques* 4(5):428–432 (1986).

Bashkin et al., "Synthesis and Characterization of Oligonucleotide Peptides," *J. Am. Chem. Soc.* 56:3168–3176 (1991).

Borchardt and Still, "Synthetic Receptor Binding Elucidated with an Encoded Combinatorial Library," *J. Am. Chem. Soc.* 116:373–374 (1994).

Brenner and Lerner, "Encoded Combinatorial Chemistry," *Proc. Natl. Acad. Sci. USA* 89:5381–5383 (1992).

Crick et al., "Codes Without Commas," *Proc. Natl. Acad. Sci. USA* 43:416–421 (1957).

Cwirla et al., "Peptides on Phage: A Vast Library of Peptides for Identifying Ligands," *Proc. Natl. Acad. Sci. USA* 87:6378–6382 (1990).

Eritja et al., "Synthesis of Defined Peptide–Oligonucleotide Hybrids Containing a Nuclear Transport Signal Sequence," *Tetrahedron* 47(24):4113–4120 (1991).

Fodor et al., "Light–Directed, Spatially Addressable Parallel Chemical Synthesis," *Science* 251:767–773 (1991).

Frank et al., "A New General Approach for the Simultaneous Chemical Synthesis of Large Numbers of Olignucleotides: Segmental Solid Supports," *Nuc. Acids. Res.* 11(13):4365–4377 (1983).

Frank et al., "Facile and Rapid 'Spot–Synthesis' of Large Numbers of Peptides on Membrane Sheets," *Peptides 1990* (Giralt and Andreu, eds., ESCOM Science Pub.) pp. 151–152 (1991).

Frank and Doring, "Simultaneous Multiple Peptides Synthesis Under Continuous Flow Conditions on Cellulose Paper Discs as Segmental Solid Supports," *Tetrahedron* 44:6031–6040 (1988).

Furka et al., "More Peptides by Less Labour," *Xth Intl. Symp. Med. Chem. in Budapest, Hungary* Abstract No. P–168 (1988).

Furka et al., "Proteins and Nucleic Acids in Three Dimensions," *14th Intl. Congress Biochem. in Prague, Czechoslovakia* Abstract No. FR:013 (1988).

(List continued on next page.)

Primary Examiner—Mindy Fleisher
Assistant Examiner—James Ketter
Attorney, Agent, or Firm—Kevin Kaster; Vern Norviel; Lauren L. Stevens

[57] ABSTRACT

A general stochastic method for synthesizing compounds can be used to generate large collections of tagged compounds that can be screened to identify and isolate compounds with useful properties.

14 Claims, 1 Drawing Sheet

OTHER PUBLICATIONS

Furka et al., "Simultaneous Multiple Peptide Synthesis Under Continuous Flow Conditions on Cellulose Paper Discs as Segmental Solid Supports," *Int. J. Peptide Protein Res.* 37:487–493 (1991).

Geysen et al., "Use of Peptide Synthesis to Probe Viral Antigens for Epitopes to a Resolution of a Single Amino Acid," *Proc. Natl. Acad. Sci.* USA 81:3998–4002 (1984).

Geysen et al., "Strategies for Epitope Analysis Using Peptide Synthesis," *J. Immunol. Meth.* 102:259–274 (1987).

Haralambidis et al., "The Synthesis of Polyamide–Oligonucleotide Conjugate Molecules," *Nuc. Acids Res.* 18(3):493–505 (1990).

Hayakawa et al., "The Allylic Protection Method in Solid–Phase Oligonucleotide Synthesis: An Efficient Preparation of Solid–Anchored DNA Oligomers," *J. Am. Chem. Soc.* 112:1691–1696 (1990).

Hodgson, "Receptor Screening and the Search for New Pharmaceuticals," *Bio./Tech.* 10:973–974 (1992).

Houghton et al., "General Method for the Rapid Solid–Phase Synthesis of Large Numbers of Peptides: Specificity of Antigen–Antibody Interaction at the Level of Individual Amino Acids," *Proc. Natl. Acad. Sci.* USA 82:5131–5135 (1985).

Houghton et al., "Generation and Use of Synthetic Peptide Combinatorial Libraries for Basic Research and Drug Discovery," *Nature* 354:84–86 (1991).

Juby et al., "Facile Preparation of 3' Oligonucleotide–Peptide Conjugates," *Tetrahedron Letters* 32(7):879–882 (1991).

Kaiser et al., "Peptide and Protein Synthesis by Segment Synthesis–Condensation," *Science* 243:187–192 (1989).

Kerr et al., "Encoded Combinatorial Peptide Libraries Containing Non–Natural Amino Acids," *J. Am. Chem. Soc.* 115:2529–2531 (1993).

Lam et al., "A New Type of Synthetic Peptide Library for Identifying Ligand–Binding Activity," *Nature* 354:82–84 (1991).

Lam et al., "Rapid Selection and Structure Determination of Acceptor Binding Ligands from a Large Synthetic Peptide Library," *12th Amer. Pep. Symp.* Abstract LW3 (1991).

Needels et al., "Generation and Screening of an Oligonucleotide–Encoded Synthetic Peptide Library," *Proc. Natl. Acad. Sci.* USA 90:10700–10704 (1993).

Nikolaiev et al., "Peptide–Encoding for Structure Determination of Nonsequencable Polymers Within Libraries Synthesized and Tested on Solid–Phase Supports," *Peptide Res.* 6(3):161–170 (1993).

Ohlmeyer et al., "Complex Synthetic Chemical Libraries Indexed with Molecular Tags," *Proc. Natl. Acad. Sci.* USA 90:10922–10926 (1993).

Tjoeng et al., "Multiple Peptide Synthesis Using a Single Support (MPS3)," *Int. J. Pept. Protein Res.* 35:141–6 (1990).

Van der Zee et al., "Efficient Mapping and Characterization of a T Cell Epitope by the Simultaneous Synthesis of Multiple Peptides," *Eur. J. Immunol.* 19:43–48 (1989).

Furka et al., 1991, Int. J. Peptides Protein Res. 37:487–493 General method for rapid synthesis of multicomponent peptide mixtures.

Needels et al., 1993, Proc. Natl. Acad. Sci. USA 90: 10700–10704 Generation and screening of an oligonucleotide–encoded synthetic peptide library.

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Tyr Gly Gly Phe Leu Arg Arg Gln Phe Lys Val Val Thr
1               5                   10

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Arg Gln Phe Lys Val Val Thr
1               5

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Thr Phe Arg Gln Phe Lys Val Thr
1               5

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Thr Thr Arg Arg Phe Arg Val Thr
1               5

( 2 ) INFORMATION FOR SEQ ID NO:5:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Thr Val Arg Gln Phe Lys Thr Thr
1               5

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Gln Val Arg Gln Phe Lys Thr Thr
1               5

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide (xi) SEQUENCE DESCRIPTION: SEQ ID NO:7:

Arg Gln Phe Arg Thr Val Gln Thr
1               5

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Lys Gln Phe Lys Val Thr Lys Thr
1               5

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Gln Gln Phe Lys Val Val Gln Thr
1               5

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Lys Gln Phe Lys Val Thr Gln Thr
1               5

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Thr Gln Phe Lys Val Thr Lys Thr
1               5

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide ( x i ) SEQUENCE DESCRIPTION: SEQ ID NO:12:

Thr Phe Arg Val Phe Arg Val Thr
1               5

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Phe Arg Arg Gln Phe Arg Val Thr
1               5

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Arg Gln Phe Lys Gln Val Gln Thr
1               5

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Gln Thr Val Thr Val Lys Lys Thr
1               5

( 2 ) INFORMATION FOR SEQ ID NO:16:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Gln Gln Val Gln Arg Gln Thr Thr
1               5

( 2 ) INFORMATION FOR SEQ ID NO:17:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Lys Thr Gln Val Val Gln Phe Thr
1               5

( 2 ) INFORMATION FOR SEQ ID NO:18:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Gln Val Thr Gln Val Arg Val Thr
1               5

( 2 ) INFORMATION FOR SEQ ID NO:19:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Phe Val Val Thr Val Arg Val Thr
1               5

( 2 ) INFORMATION FOR SEQ ID NO:20:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:20:

ATCCAATCTC TCCACATCTC TATACTATCA TCACCTATCC TATTTTTACC TCACTCACTT    60

CCATTCCAC    69

( 2 ) INFORMATION FOR SEQ ID NO:21:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:21:

ATCCAATCTC TCCAC    15

( 2 ) INFORMATION FOR SEQ ID NO:22:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (oligonucleotide)

(x i) SEQUENCE DESCRIPTION: SEQ ID NO:22:

GTGGAATGGA AGTGA 15

(2) INFORMATION FOR SEQ ID NO:23:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (i i) MOLECULE TYPE: DNA (primer)

(x i) SEQUENCE DESCRIPTION: SEQ ID NO:23:

ATCTCTATAC TATCA 15

(2) INFORMATION FOR SEQ ID NO:24:

(i) SEQUENCE CHARACTERISTICS:
      (A) LENGTH: 17 amino acids
      (B) TYPE: amino acid
      (C) STRANDEDNESS: single
      (D) TOPOLOGY: linear (i i) MOLECULE TYPE: peptide (x i) SEQUENCE DESCRIPTION: SEQ ID NO:24:

Leu Arg Arg Ala Ser Leu Gly Gly Gly Arg Arg Gln Phe Lys Val Val
1               5                   10                  15
Thr

SYNTHESIZING AND SCREENING MOLECULAR DIVERSITY

CROSS-REFERENCE

This application is a continuation-in-part of U.S. patent application Ser. No. 946,239, filed Sep. 16, 1992, which is a continuation-in-part of U.S. patent application Ser. No. 762,522, filed Sep. 18, 1991, now abandoned each of which is incorporated herein by reference.

FIELD OF THE INVENTION

The present invention relates generally to methods for synthesizing very large collections of diverse molecules and for identifying and isolating compounds with useful and desired activities from such collections. The invention also relates to the incorporation of identification tags in such collections to facilitate identification of compounds with desired properties. The invention therefore relates to the fields of chemistry, biology, pharmacology, and related fields.

BACKGROUND OF THE INVENTION

Ligands for macromolecular receptors can be identified by screening diverse collections of peptides produced through either molecular biological or synthetic chemical techniques. Recombinant peptide libraries have been generated by inserting degenerate oligonucleotides into genes encoding capsid proteins of filamentous bacteriophage and the DNA-binding protein Lac I. See Cwirla et al., 1990, *Proc. Natl. Acad. Sci. USA* 87: 6378–6382; Scott & Smith, 1990, *Science* 249: 386–390; Devlin et al., 1990 *Science* 249: 404–406; Cull et al., 1992, *Proc. Natl. Acad. Sci USA* 89: 1865–1869; and PCT publication Nos. WO 91/17271, WO 91/19818, WO 93/08278, each of which is incorporated herein by reference. These random libraries may contain more than $10^9$ different peptides, each fused to a larger protein sequence that is physically linked to the genetic material encoding it. Such libraries are efficiently screened for interaction with a receptor by several rounds of affinity purification, the selected exposition or display vectors being amplified in E. coli and the DNA of individual clones sequenced to reveal the identity of the peptide responsible for receptor binding. See also PCT publication Nos. WO 91/05058 and WO 92/02536.

Chemical approaches to generating peptide or other molecular libraries are not limited to syntheses using just the 20 genetically coded amino acids. By expanding the building block set to include unnatural amino acids and other molecular building blocks, the accessible sequence and structural diversity is dramatically increased. In several of the strategies described for creating synthetic molecular libraries, the reaction products are spatially segregated and the identity of individual library members is unambiguously defined by the nature of the synthesis See Geysen et al., 1984, *Proc. Natl. Acad. Sci. USA* 81: 3998–4002; Geysen et al, 1986, in *Synthetic Peptides as Antigens;* Ciba Foundation Symposium 119, eds. Porter, R. & Wheelan, J. (Wiley, New York) pp. 131–146; Fodor et al., 1991, *Science* 251: 767–773; U.S. Pat. No. 5,143,854; and PCT patent publication Nos. WO 84/03564; 86/00991; 86/06487; 90/15070; and 92/10092, each of which is incorporated herein by reference.

Libraries of more than 30 million soluble peptides have been prepared by the "tea-bag" method of multiple peptide synthesis. See Houghten, 1985, *Proc. Natl. Acad. Sci. USA* 82: 5131–5135; and U.S. Pat. No. 4,631,211, each of which is incorporated herein by reference. Each library is synthesized and screened as degenerate peptide mixtures in which individual amino acids within the sequence are explicitly defined. An iterative process of screening (e.g. in a competition binding assay) and resynthesis is used to fractionate these mixtures and define the most active peptides within the library. See Houghten et al., 1991, *Nature* 354: 84–86; Pinilla et al., 1992, *Peptide Research* 5: 351–358; Blake, J. & Litzi-Davis, 1992, *Bioconjugate Chem.* 3: 510–513; and PCT patent publication No. WO 92/09300, each of which is incorporated herein by reference.

Using the split-synthesis protocol of Furka et al., 1988, *Abstr. 14th Int. Congr. Biochem.,* Prague, Czech. 5: 47 (see also Furka et al., 1991, *Int J. Peptide Protein Res.* 37: 487–493; and Sebestyen et al., 1993, *Bioorg. Med. Chem. Lett.* 3: 413–418), Lam and coworkers have prepared libraries containing ~$10^6$ peptides attached to 100–200 μm diameter resin beads. See Lam et al., 1991, *Nature* 354: 82–84; Lam et al., 1993, *Bioorg. Med. Chem. Lett.* 3: 419–424; and PCT patent publication No. WO 92/00091, each of which is incorporated herein by reference. The bead library is screened by incubation with a labelled receptor: beads binding to the receptor are identified by visual inspection and are selected with the aid of a micromanipulator. Each bead contains 50–200 pmol of a single peptide sequence which may be determined directly either by Edman degradation or mass spectrometry analysis. In principle, one could create libraries of greater diversity using this approach by reducing the dimensions of the beads. The sensitivity of peptide sequencing techniques is limited to ~1 pmole, however, placing a clear limitation on the scope of direct peptide sequencing analysis. Moreover, neither analytical method provides for straightforward and unambiguous sequence analysis when the library building block set is expanded to include D- or other non-natural amino acids or other chemical building blocks.

High throughput screening of collections of chemically synthesized molecules and of natural products (such as microbial fermentation broths) has traditionally played a central role in the search for lead compounds for the development of new pharmacological agents. The remarkable surge of interest in combinatorial chemistry and the associated technologies for generating and evaluating molecular diversity represent significant milestones in the evolution of this paradigm of drug discovery. See Pavia et al., 1993, *Bioorg. Med. Chem. Left.* 3: 387–396, incorporated herein by reference. To date, peptide chemistry has been the principle vehicle for exploring the utility of combinatorial methods in ligand identification. See Jung & Beck-Sickinger, 1992, *Angew. Chem. Int. Ed. Engl.* 31: 367–383, incorporated herein by reference. This may be ascribed to the availability of a large and structurally diverse range of amino acid monomers, a relatively generic, high-yielding solid phase coupling chemistry and the synergy with biological approaches for generating recombinant peptide libraries. Moreover, the potent and specific biological activities of many low molecular weight peptides make these molecules attractive starting points for therapeutic drug discovery. See Hirschmann, 1991, *Angew. Chem. Int. Ed. Engl.* 30: 1278–1301, and Wiley & Rich, 1993, *Med. Res. Rev.* 13: 327–384, each of which is incorporated herein by reference. Unfavorable pharmacodynamic properties such as poor oral bioavailability and rapid clearance in vivo have limited the more widespread development of peptidic compounds as drugs however. This realization has recently inspired workers to extend the concepts of combinatorial organic synthesis beyond peptide chemistry to create libraries of known pharmacophores like benzodiazepines (see Bunin & Ellman, 1992, *I. Amer. Chem. Soc.* 114: 10997–10998, incorporated herein by reference) as well as polymeric molecules such as oligomeric N-substituted glycines ("peptoids") and oligocarbamates. See Simon et al., 1992, *Proc. Natl. Acad. Sci. USA* 89: 9367–9371; Zuckermann et al., 1992, *I. Amer. Chem. Soc.* 114: 10646–10647; and Cho et al., 1993, *Science* 261: 1303–1305, each of which is incorporated herein by reference.

Despite the great value that large libraries of molecules can have for identifying useful compounds or improving the properties of a lead compound, the difficulties of screening such libraries, particularly large libraries, has limited the impact access to such libraries should have made in reducing the costs of, e.g., drug discovery and development. Consequently, the development of methods for generating and screening libraries of molecules in which each member of the library is tagged with a unique identifier tag to facilitate identification of compounds (see PCT patent publication No. WO 93/06121, incorporated herein by reference; see also U.S. patent application Ser. Nos. 946,239, filed Sep. 16, 1992, and 762,522, filed Sep. 18, 1991, supra) met with great enthusiasm. In the method, products of a chemical synthesis procedure, typically a combinatorial synthesis on resin beads, are explicitly specified by attachment of an identifier tag to the beads coincident with each coupling or other product generating reaction step in the synthesis. Each tag specifies what happened in a reaction step of interest, e.g. which amino acid monomer was coupled in a particular step of a peptide synthesis procedure. The structure or identity of a compound, e.g. the sequence of a peptide, on any bead can be deduced by reading the set of tags on that bead. Ideally, such tags have a high information content, are amenable to very high sensitivity detection and decoding, and are stable to reagents used in the synthesis. The concept of an oligonucleotide-encoded chemical synthesis was also proposed by Brenner and Lerner, 1992, *Proc. Natl. Acad. Sci. USA* 89: 5181–5183, incorporated herein by reference.

The encoding method has been employed to show that, starting with an orthogonally differentiated diamine linker, parallel combinatorial synthesis can be used to generate a library of soluble chimeric peptides comprising a "binding" strand and a "coding" strand. See Kerr et al., 1993, *I. Amer. Chem. Soc.* 115: 2529–2531, incorporated herein by reference. The coupling of either natural or unnatural amino acid monomers to the binding strand was recorded by building an amino acid code comprised of four L-amino acids on the "coding" strand. Compounds were selected from equimolar peptide mixtures by affinity purification on a receptor and were resolved by HPLC. The sequence of the coding strand of individual purified molecules was then determined by Edman degradation to reveal the structure of the binding strand. An analogous peptidic coding scheme was also recently reported by Nikolaiev et al., 1993, *Peptide Research* 6: 161–170.

Constraints on the sensitivity and throughput of the Edman procedure will ultimately restrict the scope of this aspect of the encoding method to analyzing libraries of limited diversity. The use of oligonucleotide tags offers greater promise, but improved methods for synthesizing oligonucleotide-tagged molecular libraries are needed. Moreover, there remains a need for alternate methodology for synthesizing and screening very large tagged molecular libraries. The present invention meets these and other needs.

SUMMARY OF THE INVENTION

The present invention provides methods and reagents for tagging the products of combinatorial chemical processes to construct encoded synthetic chemical libraries. In one important embodiment, the invention provides a method for performing peptide and oligonucleotide synthesis on microscopic beads through an alternating and compatible synthetic procedure. The large oligonucleotide-encoded synthetic peptide library produced by this combinatorial synthesis is composed of many beads, each of which contains many copies of a single peptide (with a defined sequence) and a single-stranded DNA tag whose sequence artificially and unambiguously codes for the structure of the associated peptide. The library can be efficiently interrogated for interaction with fluorescently-labeled biological receptors by flow cytometry, and individual beads selected by exploiting the ability of FACS instrumentation to sort single beads. The DNA tag on a sorted bead is amplified by the PCR and sequenced to determine the structure of the encoded peptide ligand. The library can be used, for example, to find high affinity (nanomolar) ligands for a receptor such as an anti-peptide monoclonal antibody.

A synthetic molecular library of the invention can be produced by synthesizing on each of a plurality of solid supports a compound, the compound being different for different solid supports. The compound is synthesized in a process comprising the steps of: (a) apportioning the supports in a stochastic manner among a plurality of reaction vessels; (b) exposing the supports in each reaction vessel to a first chemical building block; (c) pooling the supports; (d) apportioning the supports in a stochastic manner among the plurality of reaction vessels; (e) exposing the supports in each reaction vessel to a chemical building block; and (f) repeating steps (a) through (e) from at least one to twenty times. Typically, substantially equal numbers of solid supports will be apportioned to each reaction vessel. In one embodiment of the method, the chemical building blocks are chosen from the set of amino acids, and the resulting compound is a peptide oligomer.

More particularly, the invention relates to certain improvements in the coupling chemistries associated with such methods. One such improvement relates to the chemistry used to remove the Fmoc protecting group from the alpha-amino group of a bead, linker, or growing peptide chain in such syntheses. Preferably, such removal is effected by treatment with 5 to 15%, preferably 10%, piperidine for 5 to 60 minutes, preferably 5 to 10 minutes, although other conditions may be employed, e.g., 15 to 30% piperidine for 5 to 30 minutes. Other improvements relate to the activation chemistry of the peptide coupling reactions, in that when certain automated instrumentation is used to perform the synthesis of an oligonucleotide tagged peptide library, the invention provides for a simple mixture of HOBt/HBTU to reduce reagent supply bottles.

In another aspect, the invention relates to methods and instrumentation for synthesizing encoded synthetic chemical libraries on beads too small to be separated on convention flow cytometry instrumentation. Such small beads allow the resulting library size to increase from the more typical range of $10^9$ to $10^{13}$ for bead based libraries up to a size of $10^{18}$ members for bead-free libraries. The invention also relates to methods for screening such libraries.

The invention also relates to methods for screening encoded synthetic libraries to identify useful compounds. In one important aspect, the invention provides important advances in the field of natural product screening relating to methods for generating, tagging, and screening natural product libraries to characterize and identify compounds with useful activity.

In another aspect, the invention relates to an improved process for rapidly and efficiently identifying a pool of compounds from a molecular library of the invention. In this method, the oligonucleotide tags from a pool of tagged compounds that exhibit a desired property (e.g., binding to a receptor) are concatemerized and cloned to facilitate sequencing of a plurality of tags in a single sequencing reaction. If the tagged compounds are peptides, and an encoding scheme based on the genetic code is employed, then one can subclone individual tags from the concatemer into other selection and expression systems, such as the plasmid and phage-based systems described in the background section above, for further analysis of the peptide.

In general, the invention provides improved methods for generating and screening molecular libraries in which the individual molecules in the library are tagged with unique, easily decoded identifier tags.

DESCRIPTION OF THE SPECIFIC EMBODIMENTS

Figure 1:
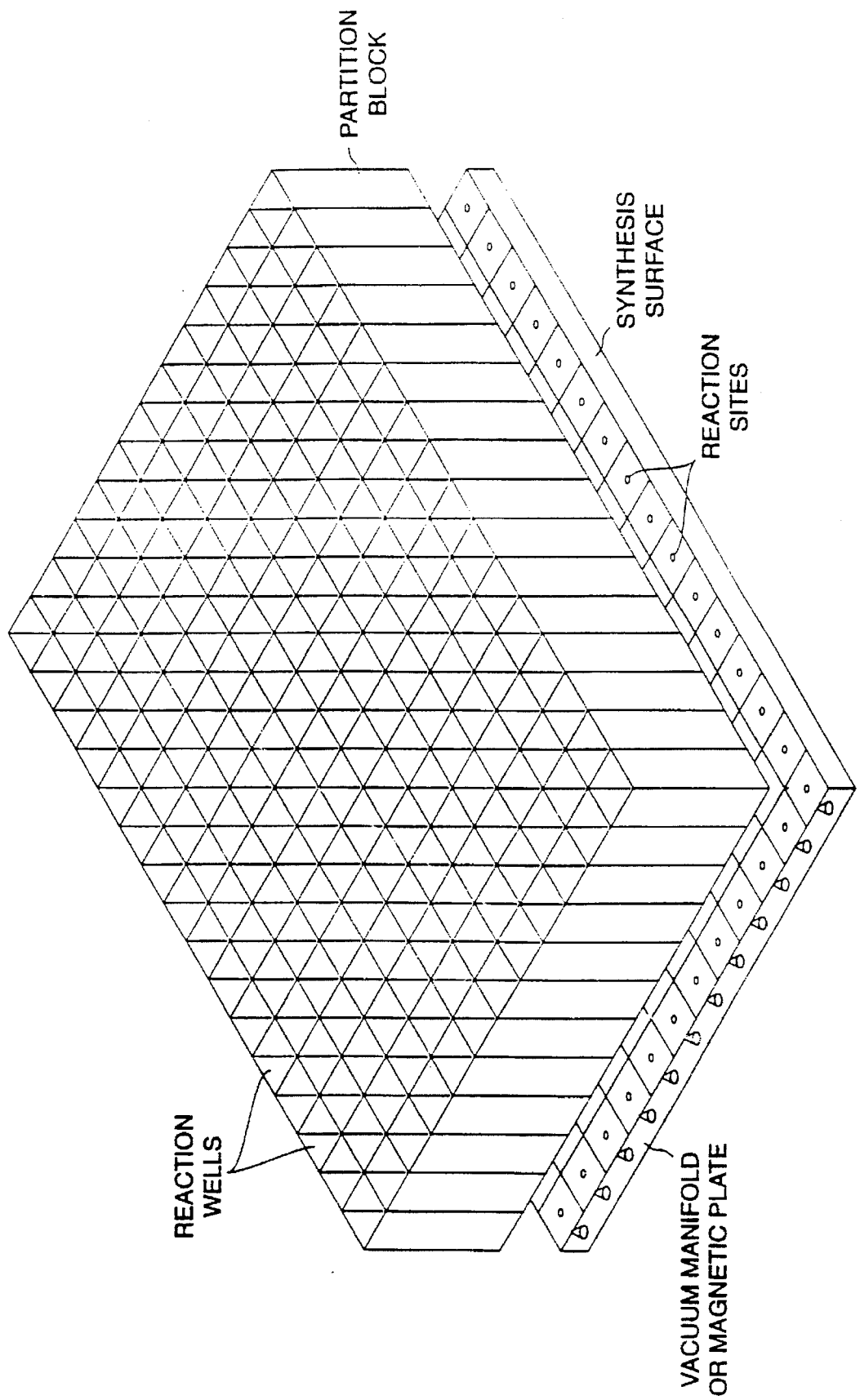
FIG. 1 shows a device for synthesizing combinatorial chemical libraries on microscopic beads. The device is composed of a vacuum manifold or magnetic plate attached to a solid substrate having a synthesis surface having an array of reaction sites at which compounds can be synthesized. The partition block is composed of an array of reaction wells corresponding to said reaction sites and is used to partition library members after each mixing step. The device can also be used to aid the synthesis of tagged chemical libraries.

The present invention relates generally to improved methods for generating and screening tagged chemical libraries. To appreciate the value of the improvements, one must understand not only the basic methodology for making and using tagged libraries but also how the various steps of synthesis and screening interact and how the selection of reagents impacts the results achieved. Tagged chemical libraries are often synthesized on a solid support, and the choice of support and linker is critical to success. A linker can be used to attach the support to the tag, to attach the support to a library molecule, or, in an embodiment where there is no solid support, to attach the tag to a library molecule. The choices relating to chemical building blocks, tags, and synthesis methods can be equally critical and are also impacted by the nature of the solid supports and linkers available. The assays and applications for which the tagged libraries are intended also impact these choices, as well as the instrumentation and reagents available. The description of the invention is therefore provided as indicated by the following outline.

OUTLINE

I. Overview of a Synthesis of a Tagged Chemical Library
II. The Solid Support
   A. Types
   B. Linkers
   C. Molecular Supports
III. The Chemical Building Blocks
   A. Oligomers and Monomers
   B. Other Building Blocks
IV. The Tag
V. Synthesis Methods
   A. Oligonucleotide Tagged Peptide Libraries
   B. Improved Method for Synthesizing Oligonucleotide-Tagged Peptide Libraries
   C. Methods for Generating Soluble Libraries
VI. Assay Methods
   A. Screening Assays for Bead-based Libraries
   B. Screening Soluble Molecules
   C. Screening Natural Product Libraries
VII. Instrumentation and Reagents
Examples
End of Outline In addition to the outline above, the following glossary is provided to facilitate the description of the invention, and a number of abbreviations and terms are defined to have the general meanings indicated as used herein to describe the invention.

Abbreviations: HBTU, O-(benzotriazol-1-yl)-1,1,3,3-tetramethyluronium hexafluorophosphate; HOBt, 1-hydroxybenzotriazole; TFA, trifluoroacetic acid; TCA, trichloroacetic acid; DIEA, diisopropylethylamine; DMF, dimethylformamide; Fmoc, 9-fluorenylmethyloxycarbonyl; DMT, dimethoxytrityl; Trt, trityl; Bz, benzoyl; Pmc, 2,2,5,7,8-pentamethylchroman-6-sulfonyl; 'Boc, tert-butyloxycarbonyl; PBS, phosphate-buffered saline; BSA, bovine serum albumin; mAb, monoclonal antibody.

Complementary or substantially complementary: These terms refer to the ability of one compound to bind to another, e.g. as a ligand binds to its complementary receptor. Typically, these terms are used in connection with a description of base pairing between nucleotides of nucleic acids, such as, for instance, between the two strands of a double stranded DNA molecule or between an oligonucleotide primer and a primer binding site on a single stranded nucleic acid to be sequenced or amplified. "Complementary" nucleotides are, generally, A and T (or A and U), and C and G, but there are a wide variety of synthetic or modified nucleotides with binding properties known to those of skill in the art. "Substantial complementarity" exists when an RNA or DNA strand will hybridize under selective hybridization conditions to a complementary nucleic acid. Typically, hybridization will occur when there is at least about 55% complementarity over a stretch of at least 14 to 25 nucleotides, but more selective hybridization will occur as complementarity increases to 65%, 75%, 90%, and 100%. See Kanehisa, 1984, *Nucl. Acids Res.* 12: 203, incorporated herein by reference. Highly selective hybridization conditions are known as "stringent hybridization conditions", defined below.

Epitope: This term is used to describe a portion of an antigen molecule delineated by the area of interaction with the subclass of receptors known as antibodies.

Identifier tag: In the most general sense, this term is used to denote a physical attribute that provides a means whereby one can identify a chemical reaction, such as a monomer addition reaction an individual solid support has experienced in the synthesis of an oligomer on that solid support. The identifier tag serves to record a step in a series of reactions used in the synthesis of a chemical library. The identifier tag may have any recognizable feature, including for example: a microscopically or otherwise distinguishable shape, size, mass, color, optical density, etc.; a differential absorbance or emission of light; chemically reactivity; magnetic or electronic properties; or any other distinctive mark capable of encoding the required information, and decipherable at the level of one (or a few) molecules. A preferred example of such an identifier tag is an oligonucleotide, because the nucleotide sequence of an oligonucleotide is a robust form of encoded information. An "identifier tag" can be coupled directly to the oligomer synthesized, whether or not a solid support is used in the synthesis. In this latter embodiment, the identifier tag can conceptually be viewed as also serving as the "support" for oligomer synthesis.

Ligand: This term is used to denote a molecule that is recognized by, typically by binding to, a particular receptor. The agent bound by or reacting with a receptor is called a "ligand", a term which is definitionally meaningful only in terms of its counterpart receptor. The term "ligand" does not imply any particular molecular size or other structural or compositional feature other than that the substance in question is capable of binding or otherwise interacting with the receptor. Also, a "ligand" may serve either as the natural ligand to which the receptor binds, or as a functional analogue that may act as an agonist or antagonist. Ligands that can be investigated by this invention include, but are not restricted to, agonists and antagonists for cell membrane receptors, toxins and venoms, viral epitopes, hormones, sugars, cofactors, peptides, enzyme substrates, cofactors, drugs (e.g., opiates, steroids, etc.), and proteins.

Monomer: This term is used to denote any member of a set of molecules that can be joined together to form another molecule or set of molecules, such as a set of oligomers or polymers. Sets of monomers useful in the present invention include, but are not restricted to, for the example of peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. Those of skill in the art will recognize that a "monomer" is simply one type of "chemical building block" and that any type of chemical building block can be employed in the present method, regardless of whether one is synthesizing an oligomer or a small organic molecule or some other molecule.

Oligomer or Polymer: These terms are used to denote molecules that are formed by a process involving the chemical or enzymatic addition of monomer subunits. Such oligomers include, for example, both linear, cyclic, and branched polymers of nucleic acids, polysaccharides, phospholipids, and peptides having either alpha-, beta-, or omega-amino acids, heteropolymers, polyurethanes, polyesters, polycarbonates, polyureas, polyamides, polyethyleneimines, polyarylene sulfides, polysiloxanes, polyimides, polyacetates, or other polymers, as will be readily apparent to one skilled in the art upon review of this disclosure.

Peptide: This term is used to denote an oligomer in which the monomers are alpha amino acids joined together through amide bonds. A "peptide" can also be referred to as a "polypeptide." In the context of this invention, one should appreciate that the amino acids may be the L-optical isomer or the D-optical isomer. Peptides are more than two amino acid monomers long, but more often are more than 5 to 10 amino acid monomers long and can be even longer than 20 amino acids, although peptides longer than 20 amino acids are more likely to be called "polypeptides." Standard single letter abbreviations for amino acids are used (e.g., P for proline). These abbreviations are included in Stryer, *Biochemistry*, Third Ed. (1988), which is incorporated herein by reference.

Oligonucleotides: This term is used to denote a single-stranded DNA or RNA molecule, typically prepared by synthetic means. Oligonucleotides employed in the present invention will usually be 50 to 150 nucleotides in length, preferably from 80 to 120 nucleotides, although oligonucleotides of different length may be appropriate in some circumstances. For instance, an oligonucleotide tag can be built nucleotide-by-nucleotide in coordination with the monomer-by-monomer addition steps used to synthesize the oligomer. In addition, very short, i.e., 2 to 10 nucleotides, oligonucleotides may be used to extend an existing oligonucleotide tag to identify a monomer coupling step. Suitable oligonucleotides may be prepared by the phosphoramidite method described by Beaucage and Carruthers, 1981, *Tetr. Left.* 22: 1859–1862, or by the triester method, according to Matteucci et al., 1981, *I. Am. Chem. Soc.* 103: 3185, both incorporated herein by reference, or by other methods such as by using commercial automated oligonucleotide synthesizers.

Operably linked: This terms refers to a functional relationship between one segment of a nucleic acid and another. For instance, a promoter (or enhancer) is "operably linked" to a coding sequence if the promoter causes or otherwise positively influences the transcription of the coding sequence. Generally, operably linked means that the nucleic acid segments or sequences being linked are contiguous and, where necessary to join two protein coding regions, contiguous and in reading frame.

Receptor: This term refers to a molecule that has a specific affinity for a given ligand. Receptors may be naturally occurring or synthetic molecules. Receptors can be employed in their unaltered natural or isolated state or as aggregates with other species. Receptors may be attached, covalently or noncovalently, to other substances. Examples of receptors that can be employed in the method of the present invention include, but are not restricted to, antibodies, cell membrane receptors, monoclonal antibodies, antisera reactive with specific antigenic determinants (such as on viruses, cells, or other materials), polynucleotides, nucleic acids, lectins, polysaccharides, cells, cellular membranes, and organelles. Receptors are also known as "anti-ligands." A "ligand-receptor pair" is formed when two molecules, typically macromolecules, have combined through molecular recognition to form a complex. Other examples of receptors include, but are not restricted to specific transport proteins or enzymes essential to survival of microorganisms for which antibiotics are needed; the binding site of any enzyme; the ligand-binding site on an antibody molecule; a nucleic acid; a catalytic polypeptides as described in Lerner et at., 1991, *Science* 252: 659, incorporated herein by reference; and hormone receptors such as the receptors for insulin and growth hormone.

Substrate or Solid Support: These terms denote a material having a rigid or semi-rigid surface. Such materials will preferably take the form of small beads, pellets, disks, or other convenient forms, although other forms may be used. In some embodiments, at least one surface of the substrate can be substantially flat. A roughly spherical shape is preferred.

Stringent hybridization conditions: This phrase refers to highly selective hybridization conditions in which nucleic acids remain stably bound in association with other nucleic acids (or other segments of the same nucleic acid) only if the associated sequences are perfectly or highly (i.e., greater than 80%) complementary. Such conditions typically include salt concentrations of less than about 1M, such as less than 500 mM, and will often include salt concentrations of less than 200 mM. The hybridization temperature for oligomers will typically be greater than 22° C., such as greater than about 30° C., and will often be in excess of about 37° C. Longer fragments may require higher hybridization temperatures for specific hybridization. As other factors may dramatically affect the stringency of hybrization (such factors include base composition, length of the complementary strands, presence of organic solvents, and extent of base mismatching), the combination of factors is more important than the absolute measure of any one factor alone.

Synthetic: A compound is "synthetic" when produced by in vitro chemical or enzymatic synthesis. The synthetic libraries of the present invention may be contrasted with those in viral or plasmid vectors, for instance, which may be propagated in bacterial, yeast, or other living hosts.

I. Overview of the Synthesis of a Tagged Chemical Library

The present invention relates generally to methods for synthesizing and screening tagged chemical libraries. In essence, each "book" of a chemical library of the invention consists of a chemical or molecule of interest, a tag identifying the chemical or molecule of interest or some important aspect thereof, and a linkage between the chemical or molecule of interest and the tag. In one important embodiment, the chemical or molecule of interest is an oligomer such as a peptide, the tag is an oligomer such as a nucleic acid, and the linkage is a solid support or particles, from which oligomers and tags may optionally be cleaved, e.g. to facilitate detection or to provide a soluble library. Such libraries can be screened to isolate individual oligomers that bind to a receptor or possess some other desired property.

A general method for producing a tagged chemical library is illustrated by the production of a large, highly diverse collection of oligomers, in which each different library member is an oligomer with a unique monomer sequence relative to other library members (although the library will typically comprise duplicate "books"). Such a library or collection may contain, for example, all combinations of X different monomers in a set of monomers assembled into length n oligomers yielding, $X^n$ different compounds. The collection may also contain oligomers having different monomer units at, for example, only one or a small number of positions, while having an identical sequence at all other positions.

A general method for synthesizing such collections of oligomers typically involves a random combinatorial ("stochastic") approach and the chemical and/or enzymatic assembly of monomer units. One process comprises the steps of: (a) apportioning a plurality of solid supports among a plurality of reaction vessels; (b) coupling to the supports in each reaction vessel a first monomer and a first tag using different first monomer and tag combinations in each different reaction vessel; (c) pooling the supports; (d) apportioning the supports among a plurality of reaction vessels; (e) coupling to the first monomer a second monomer and coupling to either the solid support or to the first tag a second tag using different second monomer and second tag combinations in each different reaction vessel; and optionally repeating the coupling and apportioning steps with different tags and different monomers one to twenty or more times. Typically, substantially equal numbers of solid supports will be apportioned to each reaction vessel. Those of skill in the art recognize that the same chemical building block can be employed in different coupling steps and that the same chemical building block can be employed in more than one coupling reaction (reaction vessel) of a single coupling step.

To visualize the method more readily, one might first consider the stochastic synthesis of an untagged library of all oligomers three residues in length, assembled from a monomer set of three different monomers: A, B, and C. Three aliquots of beads are apportioned among three reaction vessels, and monomer A is coupled to the beads in the first reaction vessel, B is coupled in the second, and C in the third. The beads from all the reaction vessels are then pooled. The pool contains approximately equal numbers of three different types of beads, with each type characterized by the monomer coupled to the bead. The pool is mixed and redistributed to the separate monomer reaction vessels, each containing A, B, or C as the next monomer to be coupled.

Following this coupling reaction, each reaction vessel now has beads with all three different monomers in position one and the monomer contained in each particular second reaction vessel in position 2. All beads are pooled again, producing a mixture of beads each bearing one of the nine possible dimers. The pool is again distributed among the three reaction vessels and coupled to the three different monomers, producing the complete set of all trimers of the three monomers ($3^3$=27). As can be readily appreciated, the use of a sufficiently large number of synthesis beads helps to ensure that the set completely represents the various combinations of monomers employed in this random, stochastic, combinatorial synthesis scheme.

Modifications of this completely random approach are also possible. For example, the monomer set may be expanded or contracted from step to step; or the monomer set could be changed completely for the next step (e.g., amino acids in one step, nucleosides in another step, carbohydrates in another step), if the coupling chemistry were available. A monomer unit for peptide synthesis, for example, may include single amino acids or larger peptide units, or both. One variation is to form several pools of various sequences on solid supports to be distributed among different monomer sets at certain steps of the synthesis. By this approach, one can also build oligomers of different lengths with either related or unrelated sequences, and one can fix certain monomer residues at some positions while varying the other residues, to construct oligomer frameworks wherein certain residues or regions are altered to provide diversity.

The synthesis of a tagged chemical library often involves such combinatorial synthesis steps. Because the identifier tag can be easily decoded to report the identity of each oligomer, however, tagged chemical libraries can be significantly larger and more complex than untagged libraries. In fact, the present methods for synthesizing encoded synthetic libraries of compounds makes possible the screening of large collections of non-sequenceable compounds produced by multi-step synthesis.

In particular, the use of oligonucleotide tags and oligonucleotide encryption provides a powerful mechanism for recording the structural identity of every member of vast library of tethered compounds, especially peptides, generated through a combinatorial synthesis. The methods are broadly applicable to encoding the combinatorial assembly of other non-peptidic structures, providing the parallel synthetic schemes remain orthogonal and compatible. The net outcome of a combinatorial synthesis is unambiguously defined only for a sequence of reactions that each proceed in very high yield to afford single products. This situation is approximated with standard peptide and DNA synthesis chemistries, and the resulting product structures are explicitly specified by the order of the building blocks and/or coupling reactions used in the synthesis.

However most synthetic organic reactions are more idiosyncratic, giving variable yields and frequently multiple products (such as regio- and stereoisomeric structures). Using such chemistry to synthesize combinatorial libraries on solid supports yields a mixture of products on each bead in the library. In the most general case, the encryption of a synthesis may not uniquely specify the chemical structure of an associated entity. Rather, the encryption process may more accurately be viewed to encode the exact synthetic protocol (e.g. reagents, reaction conditions, etc.) by which a member of the library was constructed. The library is screened to identify "active recipes" that then can be reproduced on a preparative scale and fractionated (if necessary) to isolate the bioactive component(s). The encoded library technologies have considerable potential to expand the scope of combinatorial chemistry and its applications to drug discovery and the development and isolation of a wide variety of useful compounds. With this overview of the synthesis of tagged molecular libraries, one can better appreciate important aspects of the invention, such as the use and choice of solid supports in library synthesis.

II. The Solid Support

A. Types

Typically, the tagged chemical libraries of the invention are composed of a collection of "solid supports", such as beads or particles. Such solid supports may be of any shape, although they will preferably be roughly spherical. The supports need not necessarily be homogenous in size, shape, or composition; although the supports usually and preferably will be uniform. In some embodiments, supports that are very uniform in size may be particularly preferred. In another embodiment, however, two or more distinctly different populations of solid supports may be used for certain purposes, i.e., the solid supports may be composed of a single particle, or two or more linked particles.

Solid supports may consist of many materials, limited primarily by capacity for derivatization to attach any of a number of chemically reactive groups and compatibility with the chemistry of oligomer or other molecular synthesis and tag attachment. Suitable support materials include glass, latex, heavily cross-linked polystyrene or similar polymers, gold or other colloidal metal particles, and other materials known to those skilled in the art. Except as otherwise noted, the chemically reactive groups with which such solid supports may be derivatized are those commonly used for solid state synthesis of the respective molecule or oligomer and thus will be well known to those skilled in the art. The term "solid support" as used herein embraces a particle with appropriate sites for oligomer synthesis and, in some embodiments, tag attachment and/or synthesis. There are various solid supports useful in preparation of the synthetic oligomer libraries of the present invention. Solid supports are commonly used for solid phase synthesis of, for example, peptides and nucleic acids and other oligomers as enumerated above, and thus are well known to those skilled in the art. The solid supports of the present invention do not include living cells, viruses, or cloning vectors such as phage vectors or plasmids.

One important aspect of the particular solid support chosen for practicing the invention is the size of the support. With enough solid supports and efficient coupling, one can generate complete sets of certain oligomers, if desired. In general, the solid support size is in the range of 1 nm to 100 µm, but a more massive solid support of up to 1 mm in size may sometimes be used. The appropriate size of the solid support depends on (1) the number of oligomer synthesis sites and identifier tag attachment sites desired; (2) the number of different compounds to be synthesized (and the number of solid supports bearing each oligomer that are needed for screening); and (3) the effect of the size of the solid supports on the specific screening strategies [e.g., fluorescence-activated cell sorters (FACS)] to be used.

As a specific example, solid supports of 1 µm in diameter may be used in the method. If each reaction vessel contains approximately 0.2 mL of solid supports, and the oligomers are synthesized from a set of 50 monomers (50 parallel reactions), then a total of 10 mL of solid supports, or approximately $10^{13}$ solid supports, would be required. If one wishes to make hexamers with these 50 monomers, then there are over $1.5 \times 10^{10}$ possible sequences, and each specific sequence would be represented on about $10^3$ solid supports. An estimated capacity of each bead, based on the capacity of commonly used peptide synthesizing resins, is about 0.1 pg of peptide per bead. By this estimation, then, each solid support would have about 100 amol or $10^8$ oligomer chains.

To improve washing efficiencies, one could employ nonporous beads or other solid supports less porous than typical peptide synthesis; however, for certain applications of the invention, quite porous beads or resins work well and are often preferable. Nonporous supports will have a lower density of growing chains, but even with a decrease in capacity of several orders of magnitude, sufficient oligomer densities can be produced for efficient screening. With the less porous supports, a greater proportion of the oligomers will be accessible for binding to the receptor during the screening process. Also, the less porous supports will reduce the carryover of tags from one reaction to the next, thus improving the accuracy of reading the dominant (correct) tags.

As noted above, another embodiment involves the use of two solid supports, such as beads, that are physically linked together, one with synthesis sites (or linkers) for the molecule or oligomer and one with attachment sites (or linkers) for the identifier tag(s). This arrangement allows the segregation of molecules or oligomers and identifier tags into discrete "zones" and permits the use of widely different chemically reactive groups and chemistries for attachment. The solid supports can be derivatized separately and then linked under conditions where all or nearly all of the synthesis solid supports will have a tag-attachment solid support in tow. The solid supports can be of different sizes, as for example a large synthesis bead with several (or many) smaller tag-attachment beads linked. In one embodiment, the first solid support will have at least one attached amino acid and the second solid support will have at least one attached nucleotide.

The mode of linking the two beads is constrained by the chemistry of oligomer synthesis. The most obvious means of linking the beads is with a heterobifunctional cross-linking agent (for examples of such agents, see *Pierce ImmunoTechnology Catalog and Handbook* pp. E10–E18 (1991)) interacting with the dominant chemically reactive groups on each species of solid support. Such cross-linking agents can serve a variety of purposes, as indicated by the following section.

B. Linkers

When bound to a solid support, the oligomer and its associated tag are usually attached to the support by means of one or more molecular linkers. The linker molecule, prior to attachment, has an appropriate functional group at each end, one group appropriate for attachment to the support and the other group appropriate for attachment to the oligomer or tag. In some embodiments, cleavable linkers will be used to facilitate an assay or detection step.

Given the wide availability of diverse linking reagents, one can link the identifier tags either to the oligomer or other library compound of interest or to the solid support or to a pre-existing tag. For instance, the identifier tag may be attached to a monomer incorporated into an oligomer or to a building block incorporated into a non-oligomeric compound. For peptidic oligomers, the side chain of a cysteine residue provides a convenient site for tag attachment. In other instances, the tag could even be attached so as to cap a small number of the oligomer chains, providing the decreased amount of net synthesis of the desired oligomer could be readily tolerated. One can attach the tag directly to the linker that binds the oligomer (or other compound of interest) to the solid support. In this embodiment, the linker has, prior to attachment, a third functional group appropriate for the attachment of the identifier tag.

One can of course incorporate a wide variety of linkers, depending upon the application and effect desired. For instance, one can select linkers that impart hydrophobicity, hydrophilicity, or steric bulk to achieve desired effects on properties such as coupling or binding efficiency. In one aspect of the invention, branched linkers, i.e., linkers with bulky side chains such as the linker Fmoc-Thr(tBu), are used to provide rigidity to or to control spacing of the molecules on a solid support in a library or between a molecule and tag in the library.

As noted above, cleavable linkers can be employed to useful effect. Preferred photocleavable linkers of the invention include 6-nitroveratryloxycarbonyl (NVOC) and other NVOC related linker compounds (see PCT patent publication Nos. WO 90/15070 and WO 92/10092; see also U.S. patent application Ser. No. 971,181, filed 2 Nov. 1992, incorporated herein by reference). In another embodiment, the linkers are nucleic acids with one or more restriction sites, so that one portion of a library member (either the tag, the oligomer or other compound of interest or both, or the solid support) can be selectively cleaved from another by the appropriate restriction enzyme. This novel nucleic acid linker illustrates the wide variety of linkers that may be employed to useful effect for purposes of the present invention.

C. Molecular Supports

As noted above, the invention can also be carried out in a mode in which there is no solid support, and the tag is attached directly (typically through a linker) to the oligomer or other molecule being synthesized. Alternatively, the oligomer or other molecule and its associated tag can be synthesized on a solid support and then cleaved or otherwise removed from the solid support prior to screening or other use. Such methods are described more fully below. Regardless of whether a solid support is present, the size and composition of the library will be determined by the number of coupling and mixing steps and the monomers or other building blocks used during the synthesis.

III. The Chemical Building Blocks

A. Oligomers and Monomers

The wide applicability of the present inventions is perhaps most readily grasped by considering the synthesis and screening of large libraries of diverse oligomers and polymers. Oligomers are polymeric compounds composed of monomers; for biological polymers, the sequence of the monomers in an oligomer often specifies important biological properties. Preferred oligomers of interest include peptides, oligonucleotides, oligo N-substituted glycines, and polycarbonates. As noted above, for purposes of the present invention a monomer is any member of a set of molecules that can be joined together to form an oligomer or polymer, i.e., amino acids, carbamates, sulfones, sulfoxides, nucleosides, carbohydrates, ureas, phosphonates, lipids, esters, combinations of the same, and the like. Thus, the monomers may be of any type that can be appropriately activated for chemical coupling or accepted for enzymatic coupling.

This method of assembling oligomers from many types of monomers requires using the appropriate coupling chemistry for a given set of monomer units or building blocks. Any set of building blocks that can be attached to one another in a step-by-step fashion can serve as the monomer set. The attachment may be mediated by chemical, enzymatic, or other means, or by a combination of any of these means. The resulting oligomers can be linear, cyclic, branched, or assume various other conformations as will be apparent to those skilled in the art.

B. Other Building Blocks

The invention is described herein primarily with regard to the preparation of molecules containing sequences of amino acids, but the invention can readily be applied to the preparation of other oligomers and to any set of compounds that can be synthesized in a component-by-component fashion, as can be appreciated by those skilled in the art. For instance, compounds such as benzodiazepines, hydantoins, and peptidylphosphonates can be prepared using the present methods (see U.S. Pat. No. 5,420,328, filed 9 Sep. 1993 (Atty. Docket No. 1021.2, to David Campbell et al.), which is a continuation-in-part of Ser. No. 081,577, filed 21 Jun. 1993, which is a continuation-in-part of Ser. No. 943,805, filed 11 Sep. 1992, each of which is incorporated herein by reference.

In one embodiment, the present method can be used to create libraries of branched polymers. While in many instances libraries of linear polymers, such as peptides, are quite useful, with more than 3–4 residues, the shape of these linear molecules becomes long and narrow. Most drugs do not have such an extended shape, perhaps due in part to the high degree of flexibility of the molecules. Branched backbone polymers can result in molecular shapes similar to known drugs. Thus, in one embodiment, the present invention relates to the incorporation of monomers with at least three functional groups to which other monomers can be attached.

If one uses such monomers exclusively, however, then the fully branched synthesis will always result in a high ratio (relative to the other monomers used in the synthesis) of the last monomer coupled. One could of course incorporate mixtures of different branching monomers to alter this ratio, but then one might have more difficulty in identifying the structure of a compound of interest, i.e., the more complex the mixture of branched monomers, the less information the tag may provide about the particular compound synthesized. In an improved method of the invention, one incorporates a mixture of two monomers—one capable of branching and one not—at each monomer coupling step, producing a library comprising a great diversity of shapes with highly informative tags. In this case, the tag would specify the monomers present at each coupling step but not whether the monomer was capable of branching. However, a simple resynthesis using only those monomers contained in the selected set of compounds from the first library would readily identify the structure of those compounds.

IV. The Tag

The identifier tag has a recognizable feature that is, for example, microscopically or otherwise distinguishable in shape, size, mass, charge, or color. This recognizable feature may arise from the optical, chemical, electronic, or magnetic properties of the tag, or from some combination of such properties. In essence, the tag serves to label a molecule and to encode information decipherable at the level of one (or a few) molecules or solid supports. By using identifier tags to track the synthesis pathway that each member of a chemical library has taken, one can deduce the structure of any chemical in the library (i.e., the sequence of monomers of any oligomer) by reading the identifier tag.

One can construct microscopically identifiable tags as small beads of recognizably different sizes, shapes, or colors, or labeled with bar codes. The tags can be "machine readable" luminescent or radioactive labels. The identifier tag can also be an encodable molecular structure. The information may be encoded in the size (the length of a polymer) or the composition of the molecule. Perhaps the best example of this latter type of tag is a nucleic acid sequence, i.e., RNA or DNA assembled from natural or modified bases.

To illustrate the role played by the tag in the synthesis and screening of a chemical library, consider for example, the use of microscopically recognizable, alphanumeric tags that are attached to each bead in an oligomer synthesis. The tag "A1" means that a bead participated in the A-monomer reaction at step 1, "C2" means that a bead participated in the C-monomer reaction at step 2, and "B3" means B-monomer was added in step 3, and so on. At the end of a 3-step synthesis, one bead would have three tags attached, e.g., A1, C2, and B3, indicating that the sequence of the peptides on the bead is ACB. This scheme requires a number of distinct identifier tags equal to at most the product of the number of different monomers and the number of synthesis steps (nine in this example). The number of identifier tags is reduced if the symbols are attached to one another in the order of the steps: A, A-C, A-C-B, in which case only as many identifier tags are needed as monomers, and the identifier tag is assembled in a way that preserves the record of what monomer was added, and in which addition step.

In another example, the tag is comprised of a variety of light-addressable molecules, such as fluorescent or phosphorescent compounds, the spectral properties of which can be changed (e.g. photobleaching) and therefore used to store information, which are used to mark each bead or other solid support in the library. In one such mode, a bead incorporates a variety of fluorophors, each of which can be selectively photobleached, and so rendered incapable of fluorescence or of diminished fluorescence. During each coupling or chemical reaction step, the bead is irradiated (or not) to photobleach (or not) one or more particular types of fluorophors, thus recording the monomer identity in the oligomer synthesized. See *Science* 255: 1213 (6 Mar. 1992), incorporated herein by reference.

The identifier tags therefore identify each monomer coupling or other reaction step that an individual library member or solid support has experienced and record the step in the synthesis series in which each monomer was added or other chemical reaction performed. The tags may be attached immediately before, during, or after the monomer addition or other reaction, as convenient and compatible with the type of identifier tag, modes of attachment, and chemistry of oligomer or other molecular synthesis. As noted above, the identifier tag can be associated with the oligomer through a variety of mechanisms, either directly, through a linking molecule, or through a solid support upon which the oligomer is synthesized. In the latter mode, one could also attach the tag to another solid support that, in turn, is bound to the solid support upon which the oligomer is synthesized. The identifier tag is added when the solid supports that have undergone a specific monomer addition or other chemical reaction step are physically together and so can be tagged as a group, i.e., prior to the next pooling step.

In some cases, of course, when only a small number of monomer units of an oligomer are varied, one may need to identify only those monomers which vary among the oligomers, as when one wants to vary only a few amino acids in a peptide. For instance, one might want to change only 3 to 6 amino acids in peptides 6 to 12 amino acids long, or one might want to change as few as 5 amino acids in polypeptides up to 50 amino acids long. One may uniquely identify the sequence of each peptide by providing for each solid support an identifier tag specifying only the amino acids varied in each sequence, as will be readily appreciated by those skilled in the art. In such cases, all solid supports may remain in the same reaction vessel for the addition of common monomer units and apportioned among different reaction vessels for the addition of distinguishing monomer units.

Synthetic oligodeoxyribonucleotides are especially preferred information-bearing identifier tags. Oligonucleotides are a natural, high density information storage medium. The identity of monomer type and the step of addition or any other information relevant to a chemical synthesis procedure is easily encoded in a short oligonucleotide sequence. Oligonucleotides, in turn, are readily amenable for attachment to a wide variety of solid supports, oligomers, linkers, and other molecules. For example, an oligonucleotide can readily be attached to a peptide synthesis bead.

One outstanding advantage inherent in using an oligonucleotide-based coding scheme is the ability to achieve tremendous levels of target amplification through the polymerase chain reaction (PCR, see *PCR Protocols: A Guide to Methods and Applications* (Innis, M, Gelland, D., Sninsky, J. and White, T., Academic Press, San Diego 1990); see also U.S. Pat. Nos. 4,683,202 and 4,965,188, each of which is incorporated herein by reference) and other nucleic acid replication and amplification techniques. Although the most commonly used in vitro DNA amplification method is PCR, suitable alternate amplification methods include, for example, nucleic acid sequence-based amplification (Compton, 1991, *Nature* 350: 91–92, incorporated herein by reference) and amplified antisense RNA (Van Gelder et al., 1988, *Proc. Nat. Acad. Sci. USA* 85: 7652–7656, incorporated herein by reference), and the self-sustained sequence replication system (3SR, see Guatelli et al., 1990, *Proc. Natl. Acad. Sci. USA* 87: 1874–1878, incorporated herein by reference). Only tiny quantities (with highly selective and efficient methods, even a single copy is sufficient) of DNA template is required for PCR, enabling one to use solid supports of microscopic dimensions and obtain larger libraries.

The use of nucleic acid tags facilitates the construction and screening of synthetic libraries that far exceed the diversity accessible through other tethered library techniques. Moreover, these libraries employ manageable quantities of bead material and can therefore be assayed for receptor binding using practical volumes of biological reagents. One improved method of the invention relates to a limiting step in the processing of ESL libraries with oligonucleotide tags—the amplification, strand separation, and sequencing of tags from individual beads. The method increases sequencing efficiency by at least an order of magnitude, and relates to the incorporation of a tag concatamerization (concatenation) step, in which a number of different tags typically amplified from a selected set of library members are ligated together prior to either cloning or sequencing of the oligonucleotide tags.

In one embodiment of the method, the amplified tags are concatenated and then cloned as linear arrays of 10 to 20 (or even more) tags in a conventional sequencing vector. Preferably, appropriate restriction sites are installed adjacent to the "coding regions" (sequences with information content) of the oligonucleotide tags; after amplifying the tags on a group of beads, the restriction sites are cut, and the fragments ligated to form concatamers. The concatamers are then cloned into an appropriate sequencing vector. Each template can then be used for bidirectional sequencing of a total of, for example, 500 to 800 bases, allowing the identification of more than at least 10 tags per template. This approach will also provide the option of avoiding the isolation of individual beads with FACS. Beads or tagged compounds can be sorted into pools, the pool of tags amplified, concatenated, and cloned for sequencing. In addition, because the requirement to manipulate individual beads is relieved, one can use beads smaller than 1 μm (typically, this size is too small for conventional FACS analysis) for library construction and screening. The selection can be conveniently accomplished by affinity purification methods (panning, magnetic beads, etc.) and the enriched pools of beads then amplified and cloned as above.

Oligonucleotide identifier tags can be assembled base-by-base before, during, or after the corresponding monomer coupling (for oligomer synthesis) or other chemical reaction step. In one case of base-by-base synthesis of an oligonucleotide tag, the tag for each step is a single nucleotide, or at most a very few nucleotides (i.e., a block of 2 to 5 nucleotides). In the block-by-block approach, encoded sets of nucleotides ("codons") of 2 to 5 to 10 or more bases are added as protected, activated blocks. Each block carries the monomer-type or other information, and the order of addition of one tag block to the next represents the order of the monomer addition or other reactions. Alternatively, the block may encode the oligomer synthesis or other reaction step number as well as the monomer-type or other building block information. This strategy preserves the order of the steps in the linear arrangement of the oligonucleotide chain grown in parallel with the oligomer. To preserve the chemical compatibility of the parallel synthetic steps (oligonucleotides and peptides, for example), one can modify the standard synthesis chemistries, an important aspect of the present invention discussed in further detail below.

One can also attach protected (or unprotected) oligonucleotides containing amplification primer sites, monomer-specific information, and order-of-reaction information, from 50 to 150 bases (nucleotides) in length, at each step. At the end of a series of n oligomer synthesis (monomer coupling) or other chemical synthesis steps, there would be n differently encoded sets of oligonucleotide identifier tags associated with each oligomer sequence or other chemical in the library. After identifying the oligomers with ligand activity, the associated oligonucleotides could be amplified by PCR and sequenced to decode the identity of the oligomer or other compound.

As discussed more fully below, the choice of bases used in an oligonucleotide identifier tag is dictated by the chemistry of oligomer synthesis or other chemical reaction conditions to which the tag will be exposed. For example, the use of strong acid can depurinate nucleic acids. Therefore, when chemistries requiring the use of strong acid are employed, the use of an oligonucleotide composed of only the pyrimidines C and T and a binary code can prove of value. In similar fashion, the lability of purine nucleotides to strong acid may be overcome through the use of the purine nucleoside analogs, such as 7-deaza-2'-deoxyadenosine and 7-deaza-2'-deoxyguanosine (see Barr et al., 1986, *BioTechniques* 4: 428–432, and Scheit, *Nucleotide Analogs: Synthesis and Biological Function* pp. 64–65 (John Wiley and Sons, New York), both of which are incorporated herein by reference). Use of these or other analogs would permit the use of a quaternary or other, as opposed to a binary, encoding scheme. Thus, in a preferred embodiment, the identifier tag will be an oligonucleotide about 50 to 150 nucleotides in length and composed of pyrimidines or pyrimidines and purine analogs or any type of nucleoside that will not degrade under the coupling conditions used to assemble the oligomer library. The oligonucleotide identifier tag may contain a 5' and a 3' amplification site, and optionally a DNA sequencing primer site, which may be specific for each step of the oligomer synthesis.

Encoding a combinatorial synthetic procedure with oligonucleotides provides a mechanism for addressing the major limitations of ambiguity and sensitivity encountered in the direct structural analysis of minute quantities of ligands isolated from large libraries. The high capacity of DNA for information storage can be exploited to archive the precise details of a library's construction. In Example 1 below, a "codon" structure of 2 contiguous nucleotides comprising three bases ($c^7dA$, dC, T), capable of encoding a synthesis incorporating up to $3^2=9$ amino acid building blocks was used (only seven building blocks were used in the synthesis of this library). If $c^7dG$ was also included in the coding template, then a combinatorial synthesis employing 1000 different monomers could be accomodated by using a "codon" size of just 5 nucleotides ($4^5=1024$).

Information may be encoded in the length rather than, or in addition to, the sequence of the oligonucleotide, or for that matter any other polymeric or oligomeric, tag. If only length is utilized to represent each specific monomer addition to the oligomer, then the identity of the oligomer can be decoded by, for example, amplifying an oligonucleotide tag, as described above, and identifying the tags through any of a variety of size-separation techniques, including polyacrylamide gel or capillary gel electrophoresis. Each different monomer added at a given step in an oligomer synthesis or each different chemical reaction step is represented by an oligonucleotide tag of unique length. The oligonucleotide tag contains amplification sites, such as PCR priming sequences, the sequences of which are designed to be characteristic of the given step-number in the oligomer or other chemical synthesis. Determination of the oligomer composition at any given position in the sequence then involves amplifying the tag using the PCR priming sequence characteristic for that step in the synthesis and size-separating the amplification products utilizing techniques well known in the art, such as gel or capillary electrophoresis (using the tagging oligonucleotides as standards) This embodiment is particularly useful when one desires to make a library of compounds related to a lead sequence. One need only tag during steps in which a site being analoged is synthesized.

In addition to length, oligomer sequence information can also be encoded in the sequence of bases comprising the oligonucleotide tag. This type of encryption is of value not only in the embodiment in which one attaches a different oligonucleotide tag at each coupling step but also in the embodiment in which one extends a pre-existing oligonucleotide tag at each coupling step. For example, one may use oligonucleotides of up to about 100 bases (or somewhat longer), each having seven (or more) regions, as described below.

Region 1 is a 3'-PCR primer site (20 to 25 bases). This site is used in conjunction with another PCR site (at the 5'-end of the oligonucleotide) to prime amplification by PCR. Other amplification methods may also be used.

Region 2 is a "step-specific" DNA sequencing primer site (15–20 bases). This site is specific for the particular numbered step in the synthesis series. All the oligonucleotides added to all the beads at a particular step will have this sequence in common. Each numbered step will have a highly specific primer site representing that step.

Region 3 is a spacer (20–30 bases). A spacer segment of variable length, but preferably 20 to 30 bases long, places the coding site sufficiently distant from the sequencing primer site to give a good "read" through the monomer encoding or identification region.

Region 4 is a monomer identification region (8 bases). In this illustrative embodiment, each base in the 8-bit string represents one bit of binary code, where, for example, T=0 and C=1. Each set of step-specific identifier tags consists of 8 bases with a 1 (C) or a 0 (T) at each of the 8 positions. These may be thought of as switches set to "on" or "off" at the different positions. Each monomer type is encoded by a mixture of 1 to 8 of these "switches."

Region 5 is a step number confirmation region (4 bases plus 2 bases on either side for region distinction). Four bits in this short stretch encode the step number. This is redundant to the sequencing primer but can be used to confirm that the proper primers were used and that the right step is decoded.

Region 6 is a repeat of the monomer identification region (8 bases). This region has the same information as region 4, and is used to confirm monomer identity. Installing this second monomer encoding region also increases the probability that a good sequencing "read" will be obtained.

Region 7 is a 5'-PCR primer site (20 to 25 bases). This site serves as a site for annealing the second PCR primer for amplification of the sequence. The length of oligonucleotides with all seven of these features, some of which are optional, will commonly be between 75 and 125 bases.

An 8 bit format can encode 256 different monomer types. The number of steps that can be encoded is determined by the number of step-specific sets (8 per set) of oligonucleotides on hand. With 10 sets (80 oligonucleotides) one can encode up to 256 different monomers assembled into oligomers up to 10 units long (thus providing encoding capability for up to $256^{10}=1.2\times10^{24}$ oligomer sequences). The coded identifier tags may be used so that each monomer is assigned a specific binary number (e.g., Ala=00000001, Gly=00000110, etc.). The appropriate oligonucleotides are combined to give the correct binary code.

To facilitate oligonucleotide tag identification, one has a variety of options. For instance, one could read the tag directly from the bead by sequencing or hybridization. One can also amplify oligonucleotide tags to facilitate tag identification. The oligonucleotide identifier tags carried by a single solid support or oligomer can be amplified in vivo, by cloning, or in vitro, e.g., by PCR. If the limit of detection is on the order of 100 molecules, then at least 100 or more copies of each oligonucleotide tag on a bead would be required. Copies of the tag are produced, either as single stranded oligonucleotides, double-stranded nucleic acids, or mixtures of single and double-stranded nucleic acids, by any of a variety of methods, several of which are described below, and the amplified material is sequenced. In the embodiment of the invention in which a separate and distinct oligonucleotide tag is added at each monomer addition step (as opposed to extending an existing tag at each step), one can amplify all tags at once and then divide the amplified material into as many separate sequencing reactions as there were oligomer synthesis steps (employing a different sequencing primer for each type of tag). In this embodiment, one could also design the tags so that each tag could be amplified separately from the other tags by appropriate choice of primer sequences. The sequencing reactions are performed and run on a standard sequencing gel, and the oligomer sequence is deduced from the code revealed in the resulting sequence information.

An alternative strategy is to use common PCR primers and common sequencing primers (the sequencing primer may even overlap completely or partially with a PCR primer site) and identify the step by hybridization to oligonucleotide probes that are complementary to each step-specific sequence in the oligonucleotides from the bead. A single set of sequencing reactions is performed on all of the amplified oligonucleotides from a single bead, and the reaction products are run in a single set of lanes on a gel. The reaction products are then transferred to a suitable hybridization membrane and hybridized to a single step-specific probe (see Maniatis et al., Cold Spring Harbor Laboratory, Cold Spring Harbor, N.Y. (1982), which is incorporated herein by reference). After detection of the resulting signal, the probe is washed from the membrane and another step-specific probe is hybridized. One could also use the procedure described in EPO publication No. 237,362 and PCT publication No. 89/11548, each of which is incorporated herein by reference.

Parallel hybridization provides an alternative to sequential hybridization. The sequencing reactions are divided into a number of aliquots equal to the number of peptide synthesis steps and run in a separate set of lanes for each on the sequencing gel. After transfer of the reaction products to a suitable membrane, the membrane is cut to separate the sets of lanes. Each lane set is then hybridized to one of a plurality of step-specific oligonucleotide probes (see "Uniplex DNA sequencing" and "Multiplex DNA sequencing," in *Plex Luminescent Kits Product Catalog*, Bedford, Mass., 1990, incorporated herein by reference).

As noted above, a single synthesis solid support (or an attached bead bearing a tag, or in solution in a "well") may only comprise a few hundred copies of each oligonucleotide tag. These tags may be amplified, e.g., by PCR or other means well known to those skilled in the art, to provide sufficient DNA to be sequenced accurately. The ability to decode the oligomers depends on the number of available oligonucleotide identifier tags, the level of amplification that can be achieved from the available tags, and the accuracy of sequencing that amplified DNA.

If PCR amplification of an oligonucleotide identifier tag is employed, one may encounter "PCR product contamination," caused by the product of one PCR reaction contaminating a subsequent PCR reaction mixture designed to amplify other tags having the same PCR primer binding sites. One may prevent this problem by introducing lability into the product sequences and treating subsequent reactions so as to destroy potential contamination carried over from previous reactions. A specific example of this strategy, for which commercial kits are sold by PECI and Life Technologies, is to introduce dUMP into the product. Treating each new PCR reaction with uracil-N-glycosidase degrades any dU-containing DNA present, preventing amplification of the contaminant. The template DNA, which contains no dU (only dT) is not affected. Of course, the glycosidase is removed or inactivated before amplification is begun.

Some of the tags described above for peptide synthesis have the unusual characteristic of containing only pyrimidines. This means that the uracil glycosidase strategy (Perkin Elmer Cetus Instruments (PECI) Catalog, Alameda (1991), incorporated herein by reference) will work on only half of the strands produced—those containing T's (or U's). One cannot introduce dUMP into the complementary, purine-only strand; however, the purine strand is highly vulnerable to acid depurination and alkaline-mediated scission of the backbone. The combination of these treatments can greatly reduce problems with product contamination. Another approach to preventing carryover contamination involves incorporation of a restriction site (EarI could be used for polypyrimidine tags) into the oligonucleotide tag and digestion with the corresponding restriction enzyme prior to amplification of a reaction suspected of being contaminated with the tag. This method only works if the tag to be amplified will not be cleaved by the enzyme, as would generally be the case for a single stranded oligonucleotide tag.

For sequencing amplified DNA, one usually desires to generate single stranded templates. This generation may be accomplished by any of several means. One such means is asymmetric PCR, where an excess of one of the primers is used to amplify one strand to a level 10 to 100-fold higher than the other (see, for example, U.S. Pat. No. 5,066,584, incorporated herein by reference). Another means of providing a single stranded template is to by biotinylate one of the primers and purify or remove the resulting strand by adsorption to immobilized streptavidin (*Pierce Immunotechnology Catalog and Handbook,* 1991, incorporated herein by reference). Yet another means involves generation of RNA transcripts (representing only one of the strands) from an RNA polymerase promoter and sequencing the transcripts with reverse transcriptase (Sommer et al., Chapter 25, In *PCR Protocols: A Guide to Methods and Applications,* supra, incorporated herein by reference). If the tags are composed of only pyrimidine nucleotides, then all purine strands can be eliminated by acid/base treatment, leaving the pyrimidine strand for sequencing.

The use of separate sequencing primers for each step-specific oligonucleotide requires a separate, conventional sequencing reaction for each step-specific primer. Using primers that are differentially labeled would allow the identifier tags from a single solid support to be sequenced in a single reaction and run in a single lane set (2 lanes if only polypyrimidines are used; 4 lanes if 4 different bases are used) on a gel. There are now commercially available primers labeled with distinguishable fluorophores that are suitable for this purpose (ABI Catalog, incorporated herein by reference). Sets of chemiluminescent labels now distributed commercially may also be used (Bronstein et al., *BioTechniques* 8: 310–314 (1990), incorporated herein by reference).

The amplified product can be easily sequenced or otherwise identified to decode the identity of the peptide or other molecule on the bead or otherwise attached to the oligonucleotide tag. For this purpose, one can use any of a variety of sequencing methods, including sequencing by sequence-specific probe hybridization. DNA sequencing enzymes which may be employed in the present invention include Taq DNA polymerase, *E. coli* DNA polymerase I (or the Klenow fragment), T7 polymerase, Sequenase™ and Sequenase II™ (Modified T7 DNA polymerases), Bst DNA polymerase, and reverse transcriptase (from AMV, MMLV, RSV, etc., see *USB Enzymes for DNA Sequencing,* U.S. Biochemical Corp, 1991, Cleveland OH, incorporated herein by reference). The sequence of an oligonucleotide tag may also be identified by a high fidelity DNA hybridization technique. To this end, very large scale immobilized polymer synthesis with oligonucleotides may be useful (see PCT patent publication Nos. 92/10587 and 92/10588, each of which is incorporated herein by reference).

The choice of tag, whether the tag is an oligonucleotide or some other molecular structure, depends upon the nature of the molecules of which the library is composed and the method by which those molecules are to be synthesized, as discussed in the following section.

V. Synthesis Methods

The method of the present invention can be applied to any set of synthetic chemical reactions performed in a sequence to generate diverse compounds. While the invention is typically illustrated using chemical building blocks, more typically monomer building blocks, the general nature of the invention should be appreciated. The majority of synthetic chemical reactions proceed quite differently than the typical monomer coupling reaction; the typical organic chemical reaction gives variable yields and leads to multiple products, such as regio- and stereoisomeric structures. The present invention can be used to identify useful products of such series of chemical reactions, because one can practice the methods so that the tag encodes the protocol for synthesizing the compound instead of a particular building block coupled in a particular coupling step.

To simplify discussion, however, the invention is most readily viewed as a series of monomer coupling steps. Because the various coupling reactions of the present method can be carried out in separate reaction vessels at separate times, even building blocks, such as monomers, with very different coupling chemistries can be used to assemble the compounds of interest in a library. While the invention can be practiced by exposing solid supports to a building block and an identifier tag at the same time, or sequentially (either building block and then tag or tag and then building block), the sequential approach allows one additional flexibility with respect to coupling chemistries. In any event, the preferred arrangement for conducting coupling reactions is one in which the diverse coupling reactions are carried out in parallel.

After each parallel series of coupling steps is performed, the solid supports on which the oligomers or other compounds of the library are synthesized are pooled and mixed prior to re-allocation to the individual vessels for the next coupling step. This shuffling process produces a large library of compounds with each distinct member of the library on a distinct solid support. If each synthesis step has high coupling efficiency, then substantially all the compounds on a single solid support have the same structure or, if the compounds are oligomers, monomer sequence. That structure or sequence is determined by the synthesis pathway (type and sequence of monomer or other building block coupling reactions) for any given solid support at the end of the synthesis. The maximum length of oligomers is typically less than about 20, usually from 3 to 15 monomers in length, but in some cases a length of 8 to 12 monomers (residues) is preferred.

Given the diverse numbers of tags and building blocks suitable for use with the present invention, there are a number of chemical methods by which one can prepare chemical libraries of the invention. However, one must ensure that each coupling step, whether of tag or oligomer, does not produce unacceptable levels of unwanted reactions or destroy tags or oligomers already present on the support. In one embodiment, one ensures that only desired reactions occur by using solid supports with chemically reactive groups for tag and oligomer attachment that are protected using two different or "orthogonal" types of protecting groups. The solid supports are exposed to a first deprotection agent or activator, removing the first type of protecting group from, for example, the chemically reactive groups that serve as oligomer synthesis sites. After reaction with a first monomer, and after any optional blocking steps, the solid supports are then exposed to a second activator that removes the second type of protecting group, exposing, for example, the chemically reactive groups that serve as identifier tag attachment sites. The tag is then coupled, and these steps are repeated, typically from one to about 20 times.

A. Oligonucleotide Tagged Peptide Libraries

In one important embodiment, the present invention relates to the synthesis of large libraries of diverse peptides. While many other compounds and oligomers can be made by the method (see *Gait, Oligonucleotide Synthesis: A Practical Approach*, IRL Press, Oxford (1984); Friesen and Danishefsky, 1989, *I. Amer. Chem. Soc.* 111: 6656; and Paulsen, 1986, *Angew. Chem. Int. Ed. Engl.* 25: 212, all of which are incorporated herein by reference), techniques for solid state synthesis of peptides are particularly important and well known (see Merrifield, 1963, *I. Am. Chem. Soc.* 85: 2149–2154, incorporated herein by reference), and peptide libraries are highly useful for a variety of purposes. In the Merrifield method, an amino acid is covalently bonded to a support made of an insoluble polymer. Another amino acid with an alpha-amino protecting group is reacted with the covalently bonded amino acid to form a dipeptide. The protective group is removed, and a third amino acid with an alpha protective group is added to the dipeptide. This process is continued until a peptide of a desired length and sequence is obtained. Protective groups known to those skilled in the art may be used to prevent spurious coupling (see *The Peptides*, Vols. 1 & 3 (eds. Gross, E., and J. Meinhofer, Academic Press, Orlando (1979 & 1981), which is incorporated herein by reference) or to allow one to control coupling. Photolabile, base-labile, and acid-labile protecting groups, and combinations of the same can all be employed for various purposes of the present invention.

When the present invention is used to make and screen peptide libraries, the tag of choice is a nucleic acid. There are a variety of compatible chemistries for peptide synthesis and round by round attachment of oligonucleotide identifier tags. However, to maintain the integrity of an oligonucleotide tag during peptide synthesis, one may need to use different combinations of protecting groups and/or synthetic nucleotides to avoid degradation of the tag or the oligomer synthesized. In general, polypyrimidine oligonucleotide tags are relatively stable under typical peptide synthesis conditions, as opposed to oligonucleotide tags that contain natural purine nucleotides, but a polypyrimidine nucleotide tag may be somewhat refractory to amplification by PCR. One may need to incorporate purine bases, or analogs such as 7-deaza-deoxyadenosine, and 7-deaza-deoxyguanosine, tested for ability to withstand peptide coupling (and deprotection) conditions, into the tag to achieve a desired efficiency of amplification. For purposes of the present invention, the tag optionally may contain from 10 to 90%, more preferably 35 to 50%, and most preferably 33 to 35%, purine or purine analog nucleotides. The oligonucleotide tags may optionally incorporate a biotin or other reporter group to facilitate purification, hybridization, amplification, or detection (see *Pierce ImmunoTechnology Catalog and Handbook*, 1991, incorporated herein by reference).

Thus, in selecting the chemistries used to create an oligonucleotide-tagged peptide library of the invention, one must (1) select a solid support with appropriate functional groups; (2) select the amino acid coupling chemistry; (3) select the oligonucleotide tag coupling chemistry; (4) select the protecting groups for the various tags, monomers, and oligomers; and (5) select the deprotection and, in some embodiments, cleavage chemistry (for either the tag or peptide). Those of skill in the art recognize that not all of the above selections need be made in every case, as some applications may not present the same issues as others. For instance, one or more protecting groups may not be required for all applications. In the general case, however, each of these selections is important.

To consider factors relevant to the selection of coupling chemistries and protecting groups for the synthesis of oligonucleotide tagged peptide libraries, consider a synthesis in which commercially available Fmoc protected amino acids are coupled using standard Merrifield chemistry, and the oligonucleotide tags are coupled using standard phosphoramidite chemistry. The process can be viewed as having the following steps: (1) removal of the amino-terminal Fmoc protecting group from the linker or peptide attached to the bead; (2) coupling an Fmoc protected (the side chains may be protected as well) amino acid to the free amino group produced in step (1); (3) optional capping of unreacted free amino groups; (4) removal of the DMT protecting group from the hydroxyl group on the bead or tag to which the nucleotide tag is to be attached; (5) coupling a nucleotide phosphoramidite with a 5'-DMT protecting group as well as protecting groups on the phosphate and exocyclic amines of the bases; (6) optional capping of any unreacted free hydroxyl groups; (7) oxidation of the phosphorous of the oligonucleotide tag; and (8) deprotection of the peptide and oligonucleotide tag. Each of these steps is discussed below.

(1) Removal of the amino-terminal Fmoc protecting group from the linker or peptide attached to the bead is necessary prior to the attachment of the next amino acid monomer. Typically, treatment with 30% piperidine in DMF for about one hour is used to achieve this deprotection (see also step 8), but one aspect of the present invention relates to the use of reduced concentrations of piperidine or reduced deprotection times for the synthesis of oligonucleotide tagged peptide libraries. Piperidine may cause deprotection of methyl triester protected oligonucleotide tags, and 0-methyl phosphate protecting groups have greater base stability than the standard beta-cyanoethyl group, known to be susceptible to piperidine cleavage. Preferred Fmoc deprotection conditions of the invention are 5 to 15%, preferably 10%, piperidine for 5 to 60 minutes, preferably 10 to 20 minutes, and 15 to 30% piperidine for 15 to 30 minutes. Another treatment known to effect Fmoc removal is treatment with DBU (1,8-diazabicyclo[5.4.0]undec-7-ene), e.g., 5% DBU for 5 min. However, a report by Palom et al., *Tetr. Lett.* 34: 2195–2198, incorporated herein by reference, suggests that such treatment can result in methylation at N-3 of thymidine. While DBU-mediated Fmoc removal can be effective in some applications, the potential for base modification should be recognized.

(2) Coupling an Fmoc protected amino acid to the free amino group on the bead or peptide can be achieved using standard BOP coupling chemistry (see *The Peptides*, supra). Typically, a mixture of an Fmoc protected amino acid (110 mM), HBTU (100 mM), HOBt (100 mM), and DIEA (300 mM) in a solution composed of 1:1 DMF/DCM is employed to effect amino acid coupling. In one embodiment of the invention, however, the reaction mixture is composed of 55 mM Fmoc-protected amino acid, 50 mM HBTU, and 150 mM DIEA in a solution composed of 3:1 DMF/DCM; this embodiment is preferred for use with instruments where reagent delivery bottles may be limited. The side chains may be protected as well; Fmoc/$^t$Bu protection is preferred for most purposes, due to the commercial availability of building blocks. Other useful amino acid building blocks with side chain protection included Arg(Pmc), Gln(Trt), His(Trt), Asn(Trt), Asp(O'Bu), Glu(O'Bu), and Lys('Boc) and amino acids with side chain protecting provided by photolabile protecting groups.

(3) Optional capping of unreacted free amino groups can be achieved by treatment with acetic anhydride and 1-methyl imidazole or by other methods known in the art.

(4) Removal of the DMT protecting group from the hydroxyl group on the bead or tag to which the nucleotide tag is to be attached can be achieved by treatment with trichloroacetic acid (TCA), i.e., 1% TCA in $CH_2Cl_2$. If one uses acid-labile protecting groups on phosphates and exocyclic amines of the nucleotides (i.e., deoxycytidine, 7-deaza-deoxyadenosine, and 7-deaza-deoxyguanosine), then those groups should be sufficiently robust to resist the TCA (typically 1–3%) used in 5'-O-detritylation.

(5) Coupling a nucleotide phosphoramidite with a 5'-DMT protecting group can be achieved using standard phosphoramidite chemistry, although one must take into consideration the need for protecting groups on the phosphate oxygen as well as on the exocyclic amines of the bases of the oligonucleotide tags. For photolabile protecting groups for nucleic acids, see PCT patent publication WO 92/10092 and Baldwin et al., 1990, Tetr. Lett. 46: 6879–6884, each of which is incorporated herein by reference. As noted above, suitable phosphate protecting groups include the O-methyl and beta-cyanoethyl groups, but O-allyl and/or N-allyloxycarbonyl groups (i.e., by incorporating 3-(allyl N,N'-diisopropyl) phosphoramidites) can also be used to protect phosphate oxygens and the exocyclic amines of the nucleoside bases, respectively (see Hayakawa et al., 1990, J. Amer. Chem. Soc. 112: 1691–1696, incorporated herein by reference). Allylic protecting groups can be removed using THF containing tris (dibenzylideneacetone) dipalladium-chloroform complex, triphenylphosphine, and n-butylamine/formic acid, followed by a THF wash, an aqueous sodium N,N-diethyldithiocarbamate wash, and a water wash. Phosphoramidite coupling is mediated with agents such as 1H-tetrazole; 4-nitrophenyl tetrazole; pyridinium hydrochloride/imidazole. The latter phosphoramidite activator leads to selective 5'-O-phosphitylation at the expense of low levels of spurious reaction at nitrogen on the peptide or oligonucleotide (see Gryaznov and Letsinger, 1992, Nucleic Acids Research 20: 1879–1882, incorporated herein by reference).

(6) Optional capping of any unreacted free hydroxyl groups can be achieved by treatment with acetic anhydride and 1-methyl tetrazole or by treatment with acetic anhydride/lutidine/DMAP.

(7) Oxidation of the phosphorous of the oligonucleotide tag can be achieved by treatment with iodine and pyridine or by treatment with $I_2$, collidine, MeCN in $H_2O$. Alternatively, by employing the mild oxidant 'BuOOH for oxidation at the phosphorous, one can minimize oxidation of the amino acids methionine, tryptophan, and histidine (see Hayakawa et al., 1990, Tetr. Lett. 27:4191–4194, incorporated herein by reference).

(8) Deprotection of the peptide and oligonucleotide tag can be effected by sequential treatment with 1% TCA in dichloromethane, then with thiophenol/$NEt_3$/dioxane (1:2:2), then with ethylenediamine/EtOH (1:1) at 55 degrees C, to remove the protecting groups from the tag, and then trifluoroacetic acid (95:5 TFA/water, with cation scavengers) is used to remove acid-labile amino acid protecting groups. The lability of purine nucleotides to strong acid (e.g., TFA) can be avoided by use of phosphoramidites of the purine nucleoside analogs 7-deaza-2'-deoxyadenosine and 7-deaza-2'-deoxyguanosine (see Barr et al., 1986, Bio-Techniques 4: 428–432, and Scheit, Nucleotide Analogs: Synthesis and Biological Function pp. 64–65 (John Wiley and Sons, New York), both incorporated herein by reference).

The next section illustrates one preferred embodiment for synthesizing oligonucleotide-tagged peptide libraries.

B. Improved Method for Synthesizing Oligonucleotide-Tagged Peptide Libraries

Establishing a practical bead-based oligonucleotide-encoded peptide library methodology demands that several key technical criteria be met. These include (i) the development of mutually compatible chemistries for parallel assembly of peptides and oligonucleotides; (ii) the selection of bead material with appropriate physical characteristics; (iii) the facile isolation of small beads bearing ligands that bind a target receptor; and (iv) successful reading of the tags from a single bead, i.e., by PCR amplification and sequencing of template tag DNA from single beads. The present invention provides an improved method for synthesizing such libraries, as illustrated in this section and Example 1, which show how to use single stranded oligonucleotide tags to encode a combinatorial peptide synthesis on 10 µm diameter polystyrene beads.

In this improved method, peptides and nucleotides are assembled in parallel, alternating syntheses so that each bead bears many copies of both a single peptide sequence and a unique oligonucleotide identifier tag. The oligonucleotides share common 5'- and 3'-PCR priming sites; the beads can therefore serve as templates for the PCR. To illustrate the method, an encoded synthetic library of some $8.2 \times 10^5$ hepta-peptides was generated and screened for binding to an anti-dynorphin B monoclonal antibody D32.39 (Cull et al., 1992, Proc. Natl. Acad. Sci. USA 89: 1865–1869, incorporated herein by reference), using a fluorescence activated cell sorting (FACS) instrument to select individual beads that strongly bind the antibody. After PCR amplification of the oligonucleotide tags on sorted beads, the DNA was sequenced to determine the identity of the peptide ligands, as is described more fully below.

One important aspect of this method, which is described in additional detail in Example 1, below, is the solid support selected for synthesis of the peptide and tag. Solid supports, i.e., 10 µm diameter beads, fashioned from a macroporous styrene-divinylbenzene copolymer and derivatized with a dodecylamine linker are preferred. The amino group loading of these beads was estimated to be ~100 mmol/g by exhaustive acylation with Fmoc-glycine, followed by piperidine cleavage of the Fmoc group and spectrophotometric quantitation of the released piperidine-dibenzofulvene adduct ($e_{302}$=7,800 1 mol$^{-1}$ cm$^{-1}$). With $5 \times 10^9$ beads/g, this corresponds to a maximum peptide loading of ~20 fmole/bead. Acylation of the beads with a mixture of an appropriately protected amino acid and an omega hydroxy acid provide orthogonally differentiated amino and hydroxyl groups from which the peptide and nucleotide chains respectively can be extended. The average stoichiometry of peptide to oligonucleotide per bead is controlled by varying the ratio of amino and hydroxy acids coupled to the initial bead mass (vide infra). Test peptide syntheses (5-mers to 12-mers) on these beads equipped with a trifluoroacetic acid-cleavable Knorr linker (Bernatowicz et al., 1989, Tetr. Lett. 30: 4645–4648, incorporated herein by reference) using standard Fmoc chemistry were found to proceed with high fidelity that was indistinguishable from syntheses performed on conventional peptide synthesis resin, as determined by HPLC analysis of the crude cleaved peptide carboxamides.

Parallel synthesis strategies require the use of a set of protecting groups on the amino acids and nucleotide building blocks that are mutually orthogonal, and that each of the polymer chains be stable to the reagents used in the synthesis and deprotection of the second chain. Although, in principle, a variety of protection/deprotection schemes can be used (as discussed above), Fmoc/$^t$Bu protection on the peptide building blocks is preferred, because of the extensive commercial availability of natural and unnatural amino acids protected in this manner. However, the $^t$Bu-based peptide side chain protecting groups require treatment with strong acid (typically trifluoroacetic acid) for removal, conditions that can lead to rapid depurination of oligonucleotides containing either deoxyadenosine (dA) or 2'-deoxyguanosine (dG) (see Capon, 1969, *Chem. Rev.* 69: 407–498, incorporated herein by reference). This problem has been circumvented by using 7-deaza-2'-deoxyadenosine ($c^7$ dA) in place of dA in the template oligonucleotide tag. The glycosidic bonds of deazapurine nucleosides are resistant to acid-catalyzed hydrolysis (see Scheit, 1980, *Nucleotide Analogs: Synthesis and Biological Function* (John Wiley and Sons, New York) pp. 64–65, incorporated herein by reference), and oligonucleotides incorporating these monomers are faithfully copied by thermostable polymerases used in the PCR (see McConlogue et al., 1988, *Nucl. Acids Res.* 16: 9869, and Barr et al., 1986, *BioTechniques* 4: 428–432, each of which is incorporated herein by reference). Acid-resistant guanosine analogs can also be incorporated into the template DNA.

5'-O-dimethoxytrityl 2'-deoxynucleoside 3'-(O-methyl-N,N-diisopropyl) phosphoramidites were used in all parallel syntheses. The reagent ($I_2$/collidine/$H_2O$/acetonitrile) used to convert the nucleotide phosphite intermediates to phosphotriesters in the DNA synthesis protocol was not found to adversely affect either the readily oxidized residues Trp and Met or any of the other protected amino acids. Complete removal of the 5'-O-DMT group from the growing oligonucleotide chain was achieved in ~40 sec using 1% trichloroacetic acid (TCA) in dichloromethane, while all of the acid-labile side chain protecting groups used conventionally in Fmoc/$^t$Bu chemistry, excepting the $^t$Bu ether derivative of tyrosine, were inert to treatment with 1% TCA for 1 hour. Fmoc-Tyr(O-Bz) proved a suitable replacement in the synthesis of tyrosine-containing peptides, the O-benzoyl ester being robust towards both TCA and the piperidine used for removal of the alpha-N-Fmoc protecting group in peptide synthesis. Quantitative deprotection of the alpha-amino residues required 540 minute treatment with piperidine/DMF (10% v/v) and also resulted in partial demethylation of the protected polynucleotide phosphotriesters ($t_{1/2}$~45 min). Control experiments indicated that any aberrant phosphitylation of the resulting phosphodiester species during subsequent nucleotide chain elongation was reversed by the final oligonucleotide deprotection steps (see Lehmann et al., 1989, *Nucl. Acids Res.* 17: 2379–2390, incorporated herein by reference). At the completion of the parallel synthesis, the DNA was fully deprotected by treatment with thiophenolate (phosphate O-demethylation) then ethanolic ethylenediamine (debenzoylation of protected cytidine and 7-deazaadenine residues). These mild, anhydrous aminolysis conditions did not adversely affect protected peptide sequences (see Juby et al., 1991, *Tetr. Left.* 3: 879–882, incorporated herein by reference), which were deblocked using TFA under standard conditions.

The carboxy-terminal region of opioid peptide dynorphin B (YGGFLRRQFKVVT) (SEQ ID NO:1) has been previously shown to represent the epitope of anti-dynorphin B mAb D32.39 (see Cull et al., supra): the soluble heptapeptide RQFKVVT (SEQ ID NO:2) binds D32.39 with high affinity ($K_d$~1 nM). A parallel synthesis of this peptide and a 69 base oligodeoxynucleotide was performed on orthogonally differentiated beads bearing an acid-cleavable Fmoc-protected carboxamide (Knorr) linker. After addition of the first 20 nucleotides, the beads were treated with piperidine/DMF and the first peptide residue (Fmoc-Thr($^t$Bu)-OH) coupled to the free amines. The beads were then subjected to two cycles of phosphoramidite chemistry and coupling of the next amino acid (Fmoc-Val-OH). This process was repeated until the heptapeptide sequence and nucleotide coding region had been fully elaborated, and then the DNA was extended by a further 35 nucleotides to provide a spacer region and 5'-priming site for the PCR. The beads were finally exposed to full oligonucleotide and then peptide deprotection conditions, and the TFA supernatant containing the cleaved peptide was analyzed by reverse-phase HPLC. The HPLC results showed that the crude peptide from the parallel synthesis consists of a single major component (co-eluting with authentic RQFKVVT) (SEQ ID NO:2) and that this crude product is not significantly different from that generated in a control peptide synthesis in which no oligonucleotide chemistry occurred.

The stability to parallel synthesis chemistries of template DNA containing T, dC and $c^7$ dA was compared with an analogous target containing the standard purine nucleotide dA. Using the single bead cloning capability of a FACStar Plus cytometer, individual deprotected beads from the two syntheses were sorted into microfuge tubes and the tethered oligonucleotide template amplified through 45 cycles of the PCR. A "clean" amplification product of the expected size and nucleotide sequence was obtained only from template containing the deazapurine. Thus the integrity of this oligonucleotide was maintained through the course of a parallel peptide synthesis, demonstrating that template from a single bead can be readily amplified and sequenced.

An encoded library designed to contain 823,543 ($7^7$) different hepta-peptides attached to 10 µm beads was constructed by a combinatorial synthesis using seven amino acid building blocks Arg, Gln, Phe, Lys, Val, D-Val and Thr. Alpha-N-Fmoc-Thr(tert-butyl)-oxybenzotriazole (protected threonine) and succinimidyl 4-O-DMT-oxybutyrate residues were first coupled to all the beads to provide the orthogonally differentiated amino and hydroxyl groups for this synthesis. On average, each bead bore 20 molecules of a single peptide sequence per molecule of DNA tag. Every amino acid addition was encoded by building a characteristic dinucleotide unit, and after the seventh cycle of peptide coupling the beads were pooled, and the DNA synthesis completed. Starting with a total bead mass of 35 mg (1.75× $10^8$ beads) ensured that each peptide sequence appeared on ~200 different beads in the library. Peptide microsequencing analysis of an aliquot of the library confirmed that the seven amino acids were stochastically distributed among every position of the degenerate hepta-peptide mixture (note that L-valine and D-valine are not distinguished in the Edman degradation procedure).

The binding of mAb D32.39 to control beads and to the bead library was analyzed by flow cytometry. Beads carrying the positive control sequence RQFKVVT (SEQ ID NO:2) and a 69-mer oligonucleotide tag were strongly stained by the antibody whereas blank beads were unstained. By contrast, only a small fraction of the encoded library bound D32.39. Analysis of $10^5$ events indicated ~2% of the library stained above background levels. Significantly, this binding to D32.39 was specific for the combining site as it could be completely blocked by preincubating the mAb with soluble RQFKVVT (SEQ ID NO:2) peptide. Individual beads from the library having fluorescence intensities comparable with the positive control beads were sorted into microfuge tubes for tag amplification by PCR (beads with fluorescence in the top 0.17% of the population were collected). The amplification reactions contained dUTP and uracil DNA glycosidase to prevent carryover contamination with soluble product from previous amplifications (see Longo et al., 1990, Gene 93: 125–128, incorporated herein by reference). Nucleotide sequences were obtained from 12 sorted beads and the deduced peptide sequences are given in Table 1. Representative peptide sequences obtained from single beads having fluorescence which was not significantly above background are also tabulated for comparison.

TABLE 1

| Sequence | | Kd, nM |
|---|---|---|
| High Fluorescence Intensity Beads | | |
| (SEQ ID NO. 3) | TFRQFKVT | 0.29 |
| (SEQ ID NO. 4) | TTRRFRVT | 4.3 |
| (SEQ ID NO. 5) | TVRQFKTT | 8.8 |
| (SEQ ID NO. 6) | QvRQFKTT | 16 |
| (SEQ ID NO. 7) | RQFRTVQT | 76 |
| (SEQ ID NO. 8) | KQFKVTKT | 340 |
| (SEQ ID NO. 9) | QQFKVVQT | 370 |
| (SEQ ID NO. 10) | KQFKVTQT | 410 |
| (SEQ ID NO. 11) | TQFKVTKT | 560 |
| (SEQ ID NO. 12) | TFRvFRVT | 1400 |
| (SEQ ID NO. 13) | FRRQFRVT | not tested |
| (SEQ ID NO. 14) | RQFKQVQT | not tested |
| Low Fluorescence Intensity Beads | | |
| (SEQ ID NO. 15) | QTvTvKKT | >1 |
| (SEQ ID NO. 16) | QQVQRQTT | >0.4 |
| (SEQ ID NO. 17) | KTQvVQFT | not tested |
| (SEQ ID NO. 18) | QvTQvRVT | not tested |
| (SEQ ID NO. 19) | FVVTVRVT | not tested |

The data in Table 1 is consistent with an earlier studies demonstrating that the preferred recognition sequence of D32.39 is localized to the six amino acid fragment RQFKVV of dynorphin B (see Cull et al., supra). The positively charged residues arginine and lysine are strongly preferred in the first and fourth positions of the epitope and phenylalanine appears exclusively as the third residue of this motif. At the second position glutamine is the favored residue in this library, while the aliphatic b-branched amino acids valine (L-enantiomer only) and threonine are clearly preferred as the fifth and six residues. D-Valine appears to be best tolerated at positions outside of the consensus motif. The range of affinities of peptides that were selected ($K_d$~0.3–1400 nM) was not unexpected given the design of the binding assay: bivalent primary antibody with labelled second antibody detection. Manipulation of the binding valency (for example, by using directly labelled monovalent receptor) and the stringency of wash conditions will improve the capacity to isolate only the highest affinity ligands.

C. Methods for Generating Soluble Libraries

For some applications, one may desire a "bead-free" or "soluble" library of molecules. Soluble molecules, both tagged and untagged, can be useful for a variety of purposes, including assaying the activity of a compound (see Section VI.B, below) and amplifying a tag. There are a variety of ways one to generate soluble molecular libraries, both tagged and untagged, and to solubilize compounds, both tagged and untagged, synthesized on a solid support. Typically, cleavable linkers are employed in such methods.

For instance, and as noted above in Section II.B, cleavable linkers can be used to cleave tagged or untagged molecules from a bead or other solid support, thus solubilizing the molecule of interest. To produce a soluble tagged molecule, the cleavable linker will be attached to the bead or other solid support and have at least two functional groups: one for synthesizing the molecule of interest and the other for synthesizing the tag. Thus, the molecule and tag are synthesized attached to a common linker, which, in turn, is bound to the solid support. Once the molecule and tag are synthesized, the linker is cleaved to provide a soluble tagged molecule.

A single, planar solid support can be used to synthesize the library, and the members can be cleaved from the support prior to screening using very large scale immobilized polymer synthesis (VLSIPS™) technology. See U.S. Pat. No. 5,143,854 and PCT patent publication No. 92/10092, each of which is incorporated herein by reference. In one embodiment, an array of oligonucleotides is synthesized on the VLSIPS™ chip, and each oligonucleotide is linked to the chip by a cleavable linker, such as a disulfide (see U.S. patent application Ser. No. 874,849, filed Apr. 24, 1992, incorporated herein by reference). The oligonucleotide tag has a free functional group, such as an amine, for attachment of the molecule to be tagged, which is typically an oligomer and preferably a peptide. The tag may optionally contain only pyrimidine or pyrimidine and purine analog bases. The tag also contains binding sites for amplification, i.e., PCR primer sites, optionally a sequencing primer site, and a short section uniquely coding the monomer sequence of the oligomer to be tagged. Then, the oligomer is synthesized, i.e., from a free terminal amine groups on the tag or a linker linked to the tag, so that each oligomer is linked to a tag. The collection of tagged oligomers can be released from the chip by cleaving the linker, creating a soluble tagged oligomer library.

Other advantages can be realized by generating soluble libraries of molecules. In any bead-based library, the size (mass) of the bead will impose practical limits on the size of the library that can be assembled. For instance, several grams of beads may be required to assemble a library containing $10^9$ different tagged molecules. The present invention provides an improved method for synthesizing tagged molecular libraries that enables one to obtain much larger libraries much more practically. This improved method provides a means whereby the compounds are released from the solid support prior to the mixing steps but are reattached to the solid support prior to each coupling step.

In this method, the tagged molecule is immobilized on a solid support in a reversible manner, allowing one to release the tagged molecule from the support during each of the mixing steps of the method. In one embodiment, this reversible binding is provided by an ultrafiltration membrane (for suitable membranes, see, e.g., the "Commercial Compatibility Chart" in the Millipore catalogue, which shows membranes inert to a variety of solvents and chemicals used in synthesis methods). A membrane with a molecular weight cut-off of about 2,000 to 10,000 daltons (such as the Amicon YM5 membrane) would be suitable for most libraries. During the coupling steps, the molecules of the library would be retained by the membrane, while the coupling and other reagents would be drawn through the membrane by vacuum suction. The vacuum would be released to allow the molecules to be mixed during the mixing steps.

In another embodiment of the method, a reversible covalent linkage is used to attach the tagged molecules to the support during the coupling steps. Examples of suitable reversible chemical linkages include (1) a sulfoester linkage provided by, e.g., a thiolated tagged-molecule and a N-hydroxy-succinimidyl support, which linkage can be controlled by the $NH_2OH$ concentration; and (2) a disulfide linkage provided by, e.g., a thiolated tagged-molecule and a 2-pyridyl disulfide support (e.g., thiolsepharose from Sigma), which linkage can be controlled by the DTT (dithiothreitol) concentration.

VI. Assay Methods

The utility of large combinatorial libraries for ligand discovery depends critically on the availability of robust and affinity-sensitive biochemical assay methodologies. The present invention provides a number of novel assays for use with encoded synthetic molecular libraries, which in turn have a wide variety applications. By way of example, such libraries can be used in assays to identify ligands that bind receptors, such as peptides and nucleic acids that bind to proteins, drugs that bind therapeutic target receptors, and epitopes (both natural and synthetic) recognized by antibodies, as well as to identify a variety of compounds with pharmaceutical, agricultural, and medical diagnostic applications. Given these diverse applications, there are a wide variety of assay methods relevant to the present invention. Two important types of assays, albeit with some overlap, include bead-based assays and assays of soluble molecules.

In general, however, such assays typically involve the following steps. The libraries are screened by assays in each different molecule in the library is assayed for ability to bind to a receptor of interest. The receptor is contacted with the library of synthetic molecules, forming a bound member between the receptor and any molecule in the library able to bind the receptor under the assay conditions. The bound molecule is then identified by examination of the tag associated with that molecule. In one embodiment, the receptor to which the library is exposed under binding conditions is a mixture of receptors, each of which is associated with an identifier tag specifying the receptor type, and consequently two tags are examined after the binding assay.

A. Screening Assays for Bead-based Libraries

When specific beads are isolated in a receptor screening, the beads can be segregated individually by a number of means, including infinite dilution, micromanipulation, or preferably, flow cytometry. Libraries of tethered ligands are most effectively evaluated in binding assays with soluble labeled receptors. By adopting cell-sized solid supports or beads, one can use flow cytometry for high sensitivity receptor binding analysis and facile bead manipulation.

Flow cytometry, commonly referred to as fluorescence activated cell sorting or FACS should be viewed as equivalent to "fluorescence activated molecular sorting" or "fluorescence activated bead sorting" for purposes of the present invention. One of ordinary skill in FACS methods for cloning mammalian cells expressing cell surface antigens or receptors can readily practice the assay methods of the present invention. In general, these assays involve the binding of a receptor labelled with a fluorescent tag to a mixture of beads displaying the diverse molecules of a molecular library. After washing away unbound or non-specifically bound receptors, one then employs a FACS instrument to sort the beads and to identify and isolate physically individual beads showing high fluorescence. See *Methods in Cell Biology*, Vol. 33 (Darzynkiewicz, Z. and Crissman, H. A., eds., Academic Press); and Dangl and Herzenberg, 1982, *I. Immunol. Meth.* 52: 1-14, both incorporated herein by reference. Once the desired beads have been isolated, one identifies the tag to ascertain the identity (or molecular structure, composition, or conditions of synthesis) of the molecule of interest on the bead.

Standard FACS instrumentation permits bead (cell) fluorescence analysis rates of $\sim 10^4$ events/sec. and, when operated in single bead cloning mode, sort rates that are 5–10 fold slower. In assaying very large libraries (e.g. $\gg 10^7$ beads) some form of affinity-selective pre-screen can be used prior to individual bead isolation with the cell-sorter. For example, receptor-coated sub-micron sized superparamagnetic particles are frequently used to affinity purify specific cells from large, mixed populations by magnetic activated sorting (see Miltenyi et al., 1990, *Cytometry* 11: 231–238, incorporated herein by reference). To have a high probability of detecting very rare binding events, each different compound in the library should be present on many beads in the library. A practical upper limit for the size of an encoded library constructed from 10 μm particles, assuming a hundred-fold redundancy, is probably $10^8$–$10^9$ compounds synthesized on $\sim 10^{10}$–$10^{11}$ beads. Even larger libraries can be prepared using smaller beads, but conventional cytometers are unlikely to detect or manipulate particles much less than $\sim 1$ μm in diameter. Of course, as noted elsewhere herein, the present invention provides a variety of applications for such small beads in the synthesis and screening of libraries of molecules. For instance, by using the oligonucleotide tag concatenation method of the invention, one need not use FACS methodology to sort the molecules in the library.

Nonetheless, one should not underestimate the power of FACS instrumentation for purposes of the present invention. In one assay method of the invention, the tagged molecular library is synthesized on fluorescent beads. The beads are smaller than cells and composed of a fluorescent material. The library is incubated with a suspension of cells expressing a high level of a cell surface receptor of interest, such as a G-protein-linked receptor. Of course, one can also perform a variety of controls, such as conducting all steps with cells that do not express a high level of the cell surface protein, and use those controls to identify false positives.

In any event, cells expressing the receptor can bind to any library members presenting a ligand for the receptor. Fluorescently labeled cells can be readily distinguished and separated from fluorescent unbound library beads and from unlabeled cells with a FACS instrument based on light-scattering or another fluorescent signal, e.g., from a cell nucleus. After sorting, the tags from the beads attached to the cells are examined to identify the ligands specific for the receptor. Depending on the application, one would sort for cells expressing the highest level of the desired receptor, e.g., by selecting only the brightest cells, and would adjust the binding conditions to maximize specific binding events. To discriminate between ligands specific for the receptor of interest and those specific for other cell surface receptors, one could examine tags associated with beads binding to cells expressing high levels of the receptor of interest and cells that do not.

The methods of the present invention also enable one to use FACS instrumentation to sort tagged molecular libraries synthesized on beads much smaller than the smallest beads current FACS instrumentation are capable of sorting. In this method, encoded synthetic libraries are screened for effector activity on signal transduction pathways. The synthetic library is constructed with several modifications: (a) the beads are 1 μm or smaller and need not be sortable in the FACS, allowing rather small beads to be used in some instances; (b) the tags are oligonucleotides resistant to the intracellular environment (most particularly nuclease resistant), phosphorothioates are preferred for this purpose; and (c) the peptides (or other diverse chemical entities) are attached to the bead support via a linker that cleaves in the intracellular environment. Such linkers include linkers that can be cleaved upon the application of an external factor, such as light, that does not harm the cells and linkers labile to the intracellular environment, such as a phosphodiester bond or a disulfide bond, but in any case, the cleavable linker must be stable to the parallel synthesis process.

The library beads are introduced into the reporter cells preferably by a mechanical process such as, for example, biolistic projection. In some cases, a biochemically-mediated process leading to internalization can be employed, but this route usually results in incorporation into an undesirable cellular compartment (i.e., lysozomal localization). Once the beads are in the cells, the peptides or other compounds of interest are released. Given that 10 µm beads have a demonstrated capacity of $10^{10}$ peptide (or other) synthesis sites, then if the capacity scales with volume, a 1 µm bead of the same material would contain $10^7$ molecules of the synthesized peptide. If all of the synthesized peptide is released in a single (spherical) cell of ~10 µm diameter (a volume of ~0.5 pL), then a concentration of free peptide of ~30 µM would result. This concentration would be controllable by the synthesis density on the beads, and a lower loading density could provide for a more stringent screening format (i.e., a screen for more active compounds). The recipient cells are engineered to generate a fluorescent signal upon activation or inactivation of the pathway of interest. The individual cells producing the desired effect are selected by FACS instrumentation, and the tags, which are still attached to the beads and contained within the cells, are amplified and sequenced to identify the active synthetic compounds.

In another embodiment, large beads are employed and used to screen a population of cells that express a receptor (i.e., the enzyme beta-galactosidase) capable of generating a fluorescent or other detectable signal, i.e., by cleavage of a substrate to produce a detectable compound. The beads are then mixed with a population of the cells, which are allowed to attach to the beads. If the receptor on the cell surface is stimulated by the compound on the bead, then the detectable compound is produced, providing a basis for sorting activated cells attached to the beads from unactivated cells. One could employ appropriate reagents (i.e., free labeled or unlabeled receptor) to maximize selection of high affinity ligands.

There are of course a variety of alternatives to flow cytometry for purposes of screening and selecting for library molecules of interest. In one embodiment, an encoded synthetic library is screened for antimicrobial activity to find compounds that retard the growth or kill bacteria or any other microorganism that can be plated in two dimensions, such as virus-infected cells, many eukaryotic cells including cancer cells, and some protozoa. Large libraries of related or unrelated chemical structures can be screened against cells in agar culture by controlled release of the peptide or compound from the bead on which it was synthesized.

The steps of the method follow: (1) plate the cells of interest on agar plates; (2) overlay the cells with another layer of agar in which the beads bearing the synthesized peptide/drug are suspended at a dilution that provides for even dispersion so that individual beads can be picked, e.g., with a capillary tube, from the solid agar; (3) initiate release of the peptide/drug from the beads; (4) culture the plate to allow diffusion of the peptide/drug from the bead immobilized in agar into the surrounding agar and into the agar below containing the indicator cells; (5) read the extent to which the diffused test compounds from individual beads have affected the growth/morphology/phenotype of the indicator cells; (6) choose zones where the indicator cells exhibit the desired response (e.g., death of a bacterial lawn) and using a capillary tube or similar, pick out the zone of agar that contains the original bead from which the test drug had diffused; (7) read the tag, e.g. by PCR amplification of the encoded material on the individual bead, to determine the structure of the peptide/drug that elicited the desired response; and (8) optionally chemically synthesize the appropriate drug/peptide and verify desired effect.

There are a variety of ways to release the test compound from beads. For instance, one could partially cleave the peptides/drugs from beads using TFA and allowing cleaved peptide to dry down onto the bead surface in such a form that subsequent resuspension in water (agar) will allow release of the peptide/drug and localization of the released compound to the zone of agar around a particular bead. One could link the drug/peptide to the bead using chemistry that is sensitive to a particular change in bead environment that can be initiated upon plating onto the agar and indicator cells or after plating and agar solidification, e.g., a photosensitive linkage, a thiol sensitive linkage, a periodate sensitive linkage, etc. These chemical agents could themselves be diffused in through another thin agar overlay, if necessary. Such release chemistry must be compatible with the integrity of the test substance, integrity of the encryption on the bead, and health of the underlying indicator cells. The particular release chemistry used will also of course depend on the type of chemistry used for synthesizing the library and the nature of the indicator cells. The method is especially preferred for screening libraries of beta-lactam antibiotics for identification of new antibiotics that might kill newly evolved strains of bacteria resistant to existing beta-lactams and for screening peptide libraries of analogues of known anti-bacterial peptides such as the magainins.

Other methods can also be used to screen bead-based molecular libraries. Affinity adsorption techniques can be employed in conjunction with the libraries of the invention. For example, the mixture of beads can be exposed to a surface on which a receptor has been immobilized (see PCT patent publication No. 91/07087, incorporated herein by reference). After washing the substrate to remove unbound beads, one can then elute beads bound to the surface using conditions that reduce the avidity of the oligomer/receptor interaction (low pH, acid treatment, or base treatment, for example). The process of affinity adsorption can be repeated with the eluted beads, if desirable. These methods, and related variants, such as the use of magnetic selection, described above, can be practiced in diverse ways; for instance the solid support can be a resin packed into a chromatographic column.

In another method of the invention, libraries of "tethered" compounds are used as a source of structural diversity in a form suitable for affinity purification of families of related molecules, such as families of receptors of pharmacologic interest. In general, this method relates to the use of a tagged and tethered molecular library to screen a second library of untagged molecules. The tagged, tethered library molecule serves as an affinity purification reagent to screen complex mixtures of soluble proteins, oligonucleotides, carbohydrates, antibodies, etc. Subsequent to affinity purification, molecules that bind to the combinatorial library members are identified by elution and appropriate separation and identification methods. The combinatorial library is then divided into smaller fractions of combinatorially synthesized compounds to determine, through repeated cycles as necessary, reductively and precisely which compound(s) mediate the binding process.

In similar fashion, combinatorial chemical libraries can be used to identify and clone novel receptors. Many receptors are members of families of proteins that share sequence homology (usually reflecting divergent evolution from an ancestral parent) but exhibit differences in their specificity/ affinity for structurally related sets of ligands/cognate receptors. Each member of a receptor family ($R_n$) may represent a separate target for specific pharmacologic action and hence for drug discovery and development by virtue of their different properties, i.e., locations in the body, specificities, affinities for ligands, etc. If one identifies a receptor ($R_1$) whose binding properties are of sufficient interest so that the identification of other receptors in the same family would be beneficial, then one can employ the following method to identify receptors related to $R_1$ in their binding site properties. One first identifies a ligand that binds to $R_1$ and then creates a tagged combinatorial compound library of molecules closely related structurally to the ligand.

Next, one prepares polysome preparations from cells believed likely to express additional members of the receptor family. Such polysomes comprise ribosomes attached to mRNA with pendant receptor in various stages of protein synthesis from nascent peptide to almost fully elaborated protein. The receptor protein nearing completion of synthesis will express the specific receptor property of binding to one or more members of the combinatorial library. Using the combinatorial library tethered to solid support, affinity purification of polysomes bearing receptors with affinity for any member of the combinatorial library is performed. Such affinity purification may involve column chromatographic methods, batchwise separation of immobilized components from the liquid phase, or aqueous two phase separation methods to achieve separation of the solid phase bearing attached receptor and relevant mRNA encoding the receptor from non-adherent polysomes.

Next, one performs cDNA synthesis from the mRNAs that encode the cognate receptor population using standard technology (reverse transcriptase, etc.) and clones the eDNA population into a vector suitable for rapid sequence analysis. Dependent on prior knowledge of the receptor sequences that are likely and the degree of sequence conservation that can be anticipated, one may attempt to use PCR or another amplification to amplify the cDNAs enriched by this method. By sequence analysis of a suitable number of cDNA clones, one can identify cDNAs (whether full length or not) that show sufficient sequence homology with the sequence of the already known receptor $R_1$ to represent putative additional members of the same receptor family ($R_n$). One prepares optionally full length cDNA clones of these novel cDNAs (or relevant portions thereof, such as the portion encoding the extracellular domain of relevance to ligand binding) by standard cloning methods and expresses these cDNAs by standard methods (i.e., in eukaryotic expression systems as soluble or membrane bound proteins as appropriate). Using standard formats for testing receptor ligand interaction, one tests for binding of populations of mixed compounds from the combinatorial library or individual compounds. In this way, one can identify precisely which compound(s) from the library bind to the newly identified receptor.

Individual beads can be physically separated, for example, by limited dilution or by methods similar to those in which cells are incubated with a receptor coupled to small superparamagnetic beads and then cells expressing a ligand for the receptor are extracted using a high power magnet (see Miltenyi et al., 1990, *Cytometry* 11: 231–238 incorporated herein by reference). As noted above, magnetically selected cells can be further analyzed and sorted using FACS. Radionucleotides may also serve to label a receptor, allowing one to identify and isolate beads by selecting beads that are radioactively labeled.

B. Screening Soluble Molecules

One can also employ tagged molecular libraries to useful effect in novel assays of the invention in which a ligand is solubilized in either tagged or untagged form prior to binding to a receptor of interest. For screening very large libraries of soluble (bead-free) tagged molecules, one preferably employs affinity chromatography under conditions of weak affinity. For example, a 30 mg library of $10^{18}$ molecules can be screened with a simple 10 mL affinity chromatography column containing a few hundred μg of a receptor of interest. Oligonucleotide are preferred tags for such libraries, being readily PCR amplified and cloned into the commercially available TA cloning vector (Invitrogen, Inc.), a convenient form for storing tag information prior to analysis by DNA sequencing. In addition, oligonucleotide tags can be concatenated, as described above, allowing one to collect pools of soluble tagged molecules, clone the concatenated tags from the selected pools, and then sequence the tags to identify the desired compounds.

Soluble tagged molecules can also be screened using an immobilized receptor. After contacting the tagged molecules with the immobilized receptor and washing away non-specifically bound molecules, bound, tagged molecules are released from the receptor by any of a wide variety of methods. The tags are optionally amplified and then examined and decoded to identify the structure of the molecules that bind specifically to the receptor. A tagged oligomer in solution can be assayed using a receptor immobilized by attachment to a bead, for example, by a competition assay with a fluorescently labeled ligand. One may recover the beads bearing immobilized receptors and sort the beads using FACS to identify positives (diminished fluorescence caused by the library molecule competing with the labeled ligand). The associated identifier tag is then be amplified and decoded.

The soluble molecules of the library can be synthesized on beads and then cleaved prior to assay. In one embodiment, the microscopic beads of a molecular library are placed in very small individual compartments or wells that have been "nanofabricated" in a silicon or other suitable surface. Beads are loaded in the wells by dispersing them in a volume of loading buffer sufficient to produce an average of one bead per well. In one embodiment, the solution of beads is placed in a reservoir above the wells, and the beads are allowed to settle into the wells. Cleavage of the oligomers from the beads may be accomplished using chemical or thermal systems, but a photocleavable system is preferred. The molecules of interest can be cleaved from the beads to produce either untagged molecules in solution (the tag remaining attached to the bead) or tagged molecules in solution. In either event, the molecules of interest are cleaved from the beads but remain contained within the compartment along with the bead and the identifier tag(s).

In one embodiment, a surface or a portion of the surface of the well is coated with a receptor. Binding buffer and a fluorescently labeled known ligand for the receptor is added to the well to provide a solution phase competition assay for ligands specific for the receptor. The binding of the fluorescently labeled ligand to the receptor can in one embodiment be estimated by confocal imaging of the monolayer of immobilized receptor. Wells with decreased fluorescence on the receptor surface indicate that the released ligand competes with the labelled ligand. The beads or the tags in wells showing competition are examined to reveal the identity of the competitive ligand.

Recovery of identifier-tagged beads from positive wells may optionally be effectuated by a micromanipulator to pluck individual beads out of wells. Another mode involves the use of beads that have incorporated a fluorescent molecule, either during bead manufacture or through labeling. A laser of the appropriate wavelength is used to bleach the resident beads in only the positive wells. All the beads are then removed en masse and sorted by FACS to identify the bleached positives. The associated tags may then be amplified and decoded to identify the molecules that bind specifically to the receptor.

In another embodiment of the invention, one employs relatively large tagged beads, from which the molecules of interest are cleaved in a series of reactions. In this method, the beads are 50 to 500 μm in diameter, with capacities equivalent to 100 to 500 pmol of peptide per bead; preferably, one uses 100 μm beads with a capacity of about 200 pmol, if constructing a peptide library. The typical size of such a library is from about $10^6$ to $10^8$, preferably $10^7$ different molecules. The library is divided into about 100 pools, each containing about 100,000 beads. A certain percentage, about 25%, of the molecule of interest is cleaved from the pool, producing, in the case of a peptide library, for example, each peptide at 50 nM in a volume of 1 mL.

The cleaved pool is then tested in a competition or functional assay. One identifies the pools with the highest activity, and then retrieves the remainder of the original pool and aliquots the remainder into 100 pools of 1000 beads per pool. The process is repeated until one has a single bead, from which one reads the tag and identifies the compound of interest. This method avoids the resynthesis and frame limitations of the Houghten method and is advantageous in that the pools are random, rather than related, compounds. The chances of a mixture being active because of the cumulative potency of many low affinity related molecules is reduced.

C. Screening Natural Product Libraries

With the automated high flux assays that are now available, the present limitations in natural product screening are first, the ability to obtain and handle (dispense, dissolve, label, etc.) the samples; and second, the substantial effort required to characterize the active components of positive samples. The present invention provides methods for generating and screening natural product libraries that can provide a huge number of samples in readily screened form and to identify active components in the samples. The basis of the method is the combination of biochemical and chemical diversity with metabolic diversity from "natural products", i.e., from nature. The simplest example involves feeding collections of peptides to cultures of microorganisms. Each microbial strain might create many modified peptides (a metabolite library). Because each culture would (potentially) contain a very complex mixture of metabolites, an efficient method of screening is required.

Several approaches are available and might be orthogonally classified as factored or tagged, and soluble or tethered. For the sake of illustration, consider as the "feedstock" a library of soluble peptides. An aliquot of the library is incubated with each of the many strains typical of a microorganism fermentation screening program, and the media screened in typical fashion. Positive cultures are then incubated with subsets of the libraries and rescreened. This process of factoring continues until the input peptides generating the most active metabolites are identified. The characterization of the active metabolites then proceeds aided by the knowledge of the likely precursor molecules. Thus, the first screening identifies the active organism(s), subsequent steps identify the active precursors, and finally, the active metabolites are identified by standard analytical means.

In all its formats, however, factoring is a tedious process. Libraries produced by split synthesis and cleaved free of the resin produce soluble compounds amenable to cellular uptake and metabolism by intact organisms. However, the concentrations of the individual compounds is quite low (inversely related to the diversity of the collection), leading to inefficient enzymatic turnover and very low concentrations of the resulting metabolites. The concentrations of the compounds may be increased by producing subsets of the libraries and fermenting each subset separately with each microbial isolate. Sub-libraries are constructed by fixing one or more of the positions and randomizing the remaining positions. For example, there are 500 pentapeptide sublibraries containing all permutations of 2 fixed positions utilizing 50 building blocks. Each of these sublibraries contains 125,000 compounds. The use of tagged libraries offers a major advantage in ease and sensitivity, but requires modifications in the method of exposing the compound collections to the metabolic activities. The combinatorial feedstock need not be only peptides but could consist of any type of combinatorial chemical collections.

Oligomer and other molecular libraries can be constructed in a combinatorial process and each step encoded with identifying tags. This may be done via a direct linkage and parallel synthesis of the oligomer to the tag. If oligonucleotides are used as the tags, then the complexes will be relatively large but small enough to insert actively into the cells via liposome fusion, electroporation, solvent permeabilization, etc. Once inside, the complexes would be subject to the metabolic machinery of the cells. One would avoid the vulnerability of the oligonucleotide tags to degradation by the use of modified nucleotides and nucleotide linkages. Upon recovery of the active metabolites from the culture of from lysed cells, the samples are screened and the tags decoded to reveal the precursor compound. Scaled-up fermentation of the active organism with the active precursors should produce sufficient quantities of the active metabolites to characterize. Libraries of compounds made by an encoded combinatorial process on beads can be exposed to lysates of bacteria, fungi, plant cells, etc. With this format, the need to insert the tagged complexes into intact cells is avoided, and only a relatively few of the many molecules on the bead need be processed to be detected (e.g., in a fluorescence-activated binding asay).

Another useful method of the invention involves the utilization of the products of one microbial culture as feed for another culture. To illustrate, consider a collection of 100 different microbial isolates from large scale cultures (~1 liter). The supernatant of each culture is recovered by filtration and divided into one hundred 10 mL aliquots. Each aliquot is inoculated with one of the 100 strains and incubated. 10,000 samples (metabolites of metabolites) are thereby generated from the 100 microbial isolates. This method of combinatorial metabolism can be extended to sequential metabolism by greatly different species: subjecting the product of microbial fermentation to incubation with exotic plant lysates or incubating extracted fractions of plant tissues with fungal cultures, for example. These methods can be used in combination; any product of a chemical diversity generating method can be subjected to these sequential metabolism product exposure steps.

In another aspect of the invention, natural product diversity is screened by creating a mixture of combinatorially-tagged liposomes, each liposome preferably encapsulating only one member or a simple mixture of a natural product compound library. The invention allows for the simultaneous assay of 1000's–10,000's of chemical compounds or natural product extracts and assay of 100's of chromatographically separated fractions derived from natural product extracts that are signal-positive. In this connection, "simultaneous" means assayed together in the same tube with the cells of the readout system.

The mixture of combinatorially tagged liposomes is prepared as follows. For each individual natural product extract or chemical from an inventory, one prepares separate liposomes encapsulating the test substance in aqueous phase. A unique liposome tag is incorporated into the liposome preparation at the time of encapsulation. The liposomes can be lyophilized for long-term storage at low-temperature, a significant advantage to the collection and storage of natural product samples near the site of collection, as well as for the long term storage of the natural product extract in a form suitable for subsequent combinatorial experimentation. The lipids in the liposome preparations are preferably identical for all samples and chosen in terms of types and composition to produce unilamellar liposomes of the desired size and integrity. Agents such as trehalose can be included at the time of liposome formation to allow lyophilization and subsequent reconstitution of intact liposomes by addition of water. At the time of generation/regeneration of tagged liposomes encapsulating the extract/chemical, one can also use a high pressure technique that allows for the encapsulation of greater volume of aqueous phase than the calculated volume enclosed by the liposome. A 3–5 fold increase in volume-equivalent can be encapsulated by this pressure method, allowing greater volume of test material to be tested, hence greater signal in the cell-based readout.

Existing liposome technology allows for creation of liposomes that incorporate a high percentage (>80%) of the aqueous phase (relevant to the efficiency of use of each test substance). Unincorporated aqueous phase can be removed by diverse "wash" methods. In addition, one can create liposomes that do not leak or exchange encapsulated aqueous phase (relevant to the specificity of tagging and absence of mixing enclosed aqueous phases), as well as liposomes that do not exchange components inserted into their lipid monolayer (glycolipid/protein antigens inserted as tags cannot be exchanged).

A wide variety of tags can be employed with the method. For example, the tags can be: (a) different fluorophores with excitation and emission properties that allow the fluorophores of each to be measured in the presence of each of the others, or combinations thereof—the fluorophores can be selected to partition in the encapsulated aqueous phase or in the membrane phase of the reconstituted liposomes, facing outwards; (b) different metal cations of rare earth elements that can be distinguished individually by atomic absorption spectrometry—the rare metal atoms would be designed to partition as salts in the encapsulated aqueous phase of the reconstituted liposomes; (c) different antigens, that can be distinguished by their specific reactions with appropriate monoclonal antibodies and primary/secondary florescent detecting antibodies/fluorophores, as necessary—the antigens, borne on proteins, glycoproteins and/or glycolipids, can be selected to partition in the membrane phase of the reconstituted liposomes, facing outwards; and (d) combinations of antigens, fluorophores, and/or metal ions can greatly increase the number of possible signatures for simultaneous screening, and an additional level of tagging of different liposomes (increased numbers) can result from use of different levels of fluorophores/metal ions/antigens, such that the different "quanta" of each component in the signature mixture could be identified.

One can also employ a general fluorescent tag that shared by all liposomes that enables rapid selection of cells fused with a liposome from those that did not fuse with a liposome. This tag is distinct from any tags used in combinatorial labelling of the individual liposome preparations and is mixed in with the liposome-generating lipids, the signature tags, and the aqueous sample of drug/natural product at the time of liposome generation. One can also employ a fluorescent tag that is self-quenched at high density (i.e., in the liposome membrane) but that will exhibit fluorescence in the outer cell membrane of a cell after a liposome fusion event and lateral diffusion of the fluorophore in the cell membrane. Depending on the mode of liposome fusion with cells, one can also incorporate a fusogenic protein of viral origin, or a glycolipid, for example, that will mediate tight adhesion of liposome to cell (dependent on a lectin like adhesion process mediated by a suitable receptor incorporated as necessary into the cell line used for read out). Such an element would not affect liposome-liposome interaction (an event to be avoided) but can enhance the efficiency of liposome-cell fusion.

The method can employ a cell read-out system that utilizes a cell line that contains a reporter gene (e.g., luciterase, beta-galactosidase) downstream of a promoter that is activated in response to addition of an exogenous hormone or ligand, such as asteroid, cytokine, prostaglandin, antibody, antigen, etc. to the cells. Binding of the activating ligand to either a cell surface receptor or an intracellular receptor activates a signal cascade that leads ultimately to activation of the responsive promoter and transcription of the signal gene. Expression of the signal protein leads to generation of a signal from the individual activated cell that can be detected quantitatively. In a search for compounds that act on any part of the intracellular signal transduction cascade as antagonists, the entire population of cells can be pretreated by addition of the exogenous signal agonist (cytokine, hormone, etc.), and one measures a decrease in signal output on an individual cell basis after the liposome fusion event. In a search for compounds that act on any part of the intracellular signal transduction cascade as agonists, no exogenous signal need be added to the cells, and one can measure the appearance of a signal on an individual cell basis after the liposome fusion event.

The mixture of tagged liposomes is mixed with a very large number excess of read-out cells. Cell number excess is critical such that after liposome-cell fusion only the following products will result: (i) cells that did not fuse with a liposome; and (ii) cells that fused with one liposome (acceptor cells). Efficient mixing is essential at this step and can be performed using a continuously stirred or linear-flow cell suspension to which the liposome mixture is added at a slow rate. Fusion is initiated by standard methods such as addition of PEG or application of a high voltage. Fusion may be enhanced if necessary by inclusion of a fusogen or a ligand-receptor recognition pair into the cell-liposome membranes. The fusion step effectively adds the aqueous phase compartment of a single liposome to an acceptor cell. Hence, the aqueous natural product extract, test compound from a chemical inventory, or fraction from chromatographic separation of a natural product extract is now able to act at any point in the intracellular signal transduction pathway. The fusion step also adds the specific tags that provide the signature of the particular test compound sample to the individual acceptor cell. If those tags were in the lipid membrane of the liposome, then the tags are distributed in the outer cell membrane of the acceptor cell. Antigens at this location are accessible to panels of specific monoclonal antibodies. Rare earth metal ions that were in the aqueous phase of the particular liposome are in the acceptor cell cytoplasm. The fusion step also adds the shared liposome tag that identifies cells that acted as acceptors from those, the excess, that did not undergo a liposome fusion event. The tag can be a fluorophore that moves from the liposome membrane to the acceptor cell membrane.

The mixture of cells, cells fused to individual liposomes, and any unfused liposomes is next incubated with the exogenous ligand (e.g., in the case of testing for an antagonist) or incubated without any addition (e.g., in the case of testing for an agonist). The time of this incubation is determined using control compounds at defined concentrations and incubation times.

Preferably, one uses FACS to select compounds (cells) of interest. For instance, one can first use forward or side light scatter to sort cells (whether acceptors or not) from any unfused liposomes. Large cells can be readily separated from small liposomes. Next, one can sort cells that were liposome acceptors from those, the excess, that were not liposome acceptors. Cells that were acceptors bear the shared liposome-derived fluorescent label, whereas the non-acceptor cells are non-fluorescent with this label. This step is of course optional but, if performed as a presort, allows separation of the (typically) majority of cells that are irrelevant to subsequent analysis from the minority that were acceptors. For identification of an antagonist, one can sort on the basis of light emission from the reporter protein (e.g., beta-galactosidase or luciferase), separating the majority of fluorescence-positive cells (rendered such by addition of the exogenous ligand earlier), from the minority of fluorescence-negative cells or low fluorescence cells. The latter two cell categories result from presumed antagonist effects of compounds that were encapsulated in the particular liposomes that fused with these individual cells. For identification of an agonist, one can sort on the basis of light emission from the reporter protein, separating the majority of fluorescence-negative cells from the minority of fluorescence-positive cells. The latter cells have resulted from a presumed agonist effect of liposome-derived compounds.

In some experiments, one can sort all cells of interest according to the criteria above as a population and collect occasional cells as cloned individuals using standard FACS methods. These individual cells can be analysed as single cells for the particular tags that they bear, allowing precise identification of the particular liposome that mediated the desired effect. In other applications, one can analyse the tag distribution in the entire sorted event-positive population and dependent on the design of the experiment and particular tags that had been incorporated in samples from different times/locations/inventories, be able in a first pass to determine the diversity of tag types in the total event-positive population.

Collected single cells or populations of cells can be analysed by methods appropriate to the particular tag combinations used. Fluorescence tags can be analysed by FACS and/or traditional spectrophotometry. Antigen tags can be analysed by addition of appropriately labelled monoclonal antibodies and ELISA, FACS, radioisotopic, or luminescence assisted assays. Metal ion tags can be analysed last by atomic absorption spectrometry. After tag decoding, the tests can be repeated either with mixtures of only those liposomes that yielded a positive event on first pass or with pure liposomes of each member of interest added to separate cell samples.

These and other methods of the invention can be automated to facilitate practice of the invention, as discussed in the following section.

VII. Instrumentation

The coupling steps for some of the monomer sets (amino acids, for example) can in some embodiments require a relatively lengthy incubation time, and for this and other reasons a system for performing many monomer additions in parallel is desirable. The present invention relates to automated instrumentation for use in generating and screening encoded synthetic molecular libraries. One preferred instrument, able to perform 50 to 100 or more parallel reactions simultaneously, is described in U.S. patent application Ser. No. 08/149,675, filed herewith at even date in the name of inventors J. Sugarman et al. (Attorney Docket No. 1007.3), incorporated herein by reference. Such an instrument is capable of distributing the reaction mixture or slurry of synthesis solid supports, under programmable control, to the various channels for pooling, mixing, and redistribution.

In general, however, the instrumentation for generating synthetic libraries of tagged molecules requires plumbing typical of peptide synthesizers, together with a large number of reservoirs for the diversity of monomers and the number of tags employed and the number of simultaneous coupling reactions desired. The tag dispensing capability translates simple instructions into the proper mixture of tags and dispenses that mixture. Monomer building blocks are dispensed, as desired, as specified mixtures. Reaction agitation, temperature, and time controls are provided. An appropriately designed instrument also serves as a multichannel peptide synthesizer capable of producing 1 to 50 mgs (crude) of up to 100 specific peptides for assay purposes. See also PCT patent publication 91/17823, incorporated herein by reference.

Typical instrumentation comprises (1) means for storing, mixing, and delivering synthesis reagents, such as peptide and oligonucleotide synthesis reagents; (2) a sealed chamber into which the various reagents are delivered and inside of which the various reactions can proceed under an inert atmosphere; (3) a matrix of sealed reaction vessels; (4) means for directing the flow of reagents to the appropriate reaction vessels: (5) means for combining and partitioning small (0.1–100 μm) beads; and (6) means for washing the beads in each reaction vessel at the conclusion of each chemical reaction. The matrix of reaction vessels can have any one of several designs. For example, the vessels can be arranged in a circle so that the vessels can be made to rotate about a central axis (i.e., a centrifuge). Alternatively the vessels can be arranged in a 12×8 matrix (96-well microtiter plate format). Any arrangement amenable to accessibility by robotic delivery, aspiration, and transfer functions is useful for some applications.

The system used for combining and redistributing particles can have one of several designs. For instance, the beads can be suspended in a solvent of appropriate surface tension and density such that a robotic pipetting instrument can be used to transfer the beads to a combining vessel. After mixing, the beads can be redistributed to the reaction vessels by the same robotic pipettor. Alternatively, the beads can be combined by using a special valved reaction chamber. The valve is opened to allow solvent flow to transfer the beads to a combining vessel. After mixing, the beads are repartitioned by reversing the flow to each reaction vessel.

In another embodiment, the beads are combined using closely spaced reaction vessels with open top ends. Flooding the vessels allows the beads to mix. If the beads are magnetic, then the beads are re-partitioned by pulling the beads back down to the bottom of the vessels by application of a magnetic field. Non-magnetic beads are re-partitioned by vacuum suction through the bottom of the reaction vessels. In yet another embodiment, the beads are partitioned by distributing them on a flat surface and then restricting them to certain sectors by covering them with a "cookie-cutter" shaped device, described more fully below.

The system for washing the beads can also have one of several designs. The beads can be washed by a combination of liquid delivery and aspiration tubing. Each reaction vessel has its own set of tubing, or a single set can be used for all reaction vessels. In the latter case, the liquid delivery and aspiration lines can be mounted on a robotic arm to address each vessel individually. The beads in each vessel can be made to form a single pellet by either centrifugation or the use of magnetic beads and application of a magnetic field. One can also employ a reaction vessel with a bottom wall composed of a chemically inert membrane so that reagents can be removed from the vessels by application of a vacuum. Reagents can also be removed from each vessel by using vessels that can accommodate continuous flow through of reagents and washing solutions, i.e., a vessel with luer fittings and membranes on each end.

Any automated combinatorial instrument that relies on an individual reaction chambers, each connected to reagent delivery systems and to a "mother pot" to which the beads are pumped for pooling and from which the beads are reallocated among the reaction chambers for successive rounds of monomer addition faces a very important practical limitation. There is a wealth of monomer or other building block units, and the difficulty of partitioning beads and reagents among the potentially large number of reactions may limit such instruments to fewer than 100 separate parallel reactions.

The present invention provides an instrument that avoids the need to pump beads between chambers to mix and reallocate, simplifies reagent delivery, and allows the simple and accurate partitioning of very small numbers of tiny beads. The basic design consists of a plate with an array of reaction "sites" located on the surface; the surface may be planar or may consist of an array of shallow wells that form reaction sites. In one embodiment, there are 256 sites in a 16×16 array. Each reaction site is a spot, or well, on the surface to which a group of synthesis beads is attracted. The attractive force may be magnetism, vacuum filtration, gravity with passive mechanical sorting, or various other simple means. The beads are initially applied as a dilute slurry in a shallow reservoir evenly covering the array of reaction sites. Upon application of the attractive force, beads are concentrated at each site.

After positioning all the beads on the reaction sites, the sites are then separated by mechanical partitions to create (temporarily) the individual reaction chambers as shown in FIG. 1. A variation provides partitions permanently affixed to the surface to form shallow wells. The reaction components are delivered to each chamber, the beads released into suspension, and the reaction initiated. When desired, the beads can be reattached to the surface and the reagents removed. After all steps for a coupling cycle are completed, the chamber partitions are removed, and the beads are released into the common reservoir above the array of sites.

Mixing of the beads is caused by induced convection of the reservoir fluid, and the beads are then reattracted to the surface sites for the next round of coupling. Subsequent steps, including the wash steps, are accomplished in a similar fashion. Addition and removal of reagents is done with a combination of plumbing and automated pipetting. Addition of reaction specific reagents (monomers, for example) may be done with robotic multipipettors. Addition of common reagents and the removal of all reagents can be done with a fixed plumbing system not requiring valving at each reaction chamber. Some common steps such as washes can be done on the beads en masse, before installing or after removing the chamber partitions.

The use of large numbers of monomers or other building blocks places an additional burden on the encoding process. In one encoding scheme for oligonucleotide tags, a basis set of 1000 monomers might require a 5 base sequence to tag each reaction step; a set of more than 1024 monomers could require 6 bases to encode. To reduce the plumbing complexity of the synthesis instrument (i.e., to reduce the number of specific reaction additions), a special encoding strategy is provided by the present invention. To illustrate the method, consider an array of 16×16 reaction sites, an arrangement that allows 256 different reactions to be carried out simultaneously. To encode each reaction individually with multiple base coupling is a difficult undertaking.

The array consists of 16 rows and 16 columns, each site in the array having a unique geographical address. Each row of sites can be tagged as a group, and all 16 rows can be uniquely encoded with 2 base codons ("subcodons"). A striped template or channel block can serve to form the 16 reaction chambers for these 2-base additions (note that the bases are coupled as monomeric phosphoramidites, not as dimers). See PCT patent publication No. WO 93/09668, incorporated herein by reference. This form of addressing of the reaction sites is analogous to others; for example, an optical method can be used to label the beads, as in the striped masking process described in U.S. Pat. No. 5,143, 854, incorporated herein by reference. If a template or channel block is employed, then the template is lowered onto the synthesis surface just as is the grid template that isolates the individual reactions during synthesis of the library molecule.

The beads are not released during the tagging reaction, however, as their spatial segregation must be maintained through the next step. When the rows have been tagged with subcodons, the template is lifted, rotated 90°, and lowered to form stripes covering the columns. The 16 columns are then labelled with 2-base subcodons, resulting in the unique tagging of each of the 256 reaction addresses with a 4-base "supercodon". By identifying the reaction addresses, the supercodons also specify the monomer that was added in each reaction.

The Example that follows illustrates an improved method of the invention for making peptide libraries tagged with oligonucleotide tags.

EXAMPLE 1

LIBRARY PREPARATION AND SCREENING

This Example illustrates how the products of a combinatorial peptide synthesis on resin beads can be explicitly specified by attaching an oligonucleotide identifier tag to the beads coincident with each amino acid coupling step in the synthesis. Each tag conveys which amino acid monomer was coupled in a particular step of the synthesis, and the overall sequence of a peptide on any bead can be deduced by reading the tag(s) on that bead. The collection of beads can be screened for binding to a fluorescently-labelled anti-peptide antibody using a fluorescence activated cell sorting (FACS) instrument. Those beads to which an antibody binds tightly can be isolated by FACS, and the oligonucleotide identifiers that are attached to individual sorted beads can be amplified by the PCR. The sequences of the amplified DNAs are determined to reveal the identity of the peptide sequences which bind to the antibody with high affinity. By combining high capacity, oligonucleotide code-based information storage, amplification methodology, and fluorescence-based sorting, the present method provides a means for specifying the identity of each member of a vast library of molecules synthesized from both natural and unnatural chemical building blocks and for quickly and efficiently isolating individual beads that bear high affinity ligands for biological receptors.

In this Example, single stranded oligonucleotides are used to encode a combinatorial peptide synthesis using both L- and D-amino acid building blocks and 10 µm diameter polystyrene beads. The oligonucleotide tags have a high information content, are amenable to very high sensitivity detection and decoding, and, with the present method, are stable to reagents used in peptide synthesis. Peptides and nucleotides are assembled in parallel, alternating syntheses so that each bead bears many copies of both a single peptide sequence and a unique oligonucleotide identifier tag. The oligonucleotides share common 5'- and 3'-PCR priming sites, and thus the beads can serve as templates for the PCR. The encoded synthetic library contains about $8.2 \times 10^5$ heptapeptides and is screened for binding to an anti-dynorphin B monoclonal antibody D32.39 (see Barrett & Goldstein, 1985, *Neuropeptides* 6: 113–120, incorporated herein by reference), using a fluorescence activated cell sorting (FACS) instrument to select individual beads that strongly bind the antibody. After PCR amplification of the oligonucleotide tags on sorted beads, the DNA is sequenced to determine the identity of the peptide ligands.

A. Reagents and General Methods

The monodisperse 10 µm diameter bead material used in this work was a custom-synthesized macroporous styrene-divinylbenzene copolymer functionalized with a 1,12-diaminododecane linker purchased from Pharmacia. The beads are Pharmacia Monobeads™ that have not been derivatized with Pharmacia's Gene Assembler Support linker. See Ugelstad and Mork, 1980, *Adv. Colloid. Interface Sci.* 13: 101–140, incorporated herein by reference.

All protected amino acids were obtained from Bachem Bioscience Inc. PCR and sequencing primers were synthesized with an Applied Biosystems model 394 oligonucleotide synthesizer. Authentic samples of certain peptides were synthesized with an Applied Biosystems model 431A peptide synthesizer using Fmoc-protected amino acids, HBTU/HOBt in situ activation chemistry, and deprotection with 40:1:1 TFA/water/ethanedithiol. These peptides were purified by HPLC (>95% purity) on a Rainin $C_{18}$ reverse phase column using water/acetonitrile/0.1% TFA as eluant, and structures were verified by mass spectrometry.

B. Parallel Synthesis of a 69-base Oligonucleotide and the Opioid Peptide Dynorphin B The C-terminal seven amino acid fragment of the opioid peptide dynorphin B H-Arg-Gln-Phe-Lys-Val-Val-Thr-NH$_2$ (RQFKVVT) (SEQ ID NO:2) was synthesized in parallel with a 69-mer oligodeoxynucleotide (ST08) on 10 µm diameter beads. The sequence of ST08 was 5'-ATC CAA TCT CTC CAC (ATC TCT ATA CTA TCA) TCA CC [TA TC CT AT TT TT AC] CTC ACT CAC TTC CAT TCC AC-3' (SEQ ID NO:20). Underlined portions of this sequence correspond to PCR-priming sites while the region in parentheses is homologous to the primer used for sequencing this template. The 14-base sequence enclosed in brackets represents the coding region of the template.

The beads were first treated with a mixture of succinimidyl 4-O-DMT-oxybutyrate (Molecular Probes) and the 1-oxybenzotriazole ester of either N-Fmoc-2,4-dimethoxy-4'-(carboxymethyloxy)-benzhydrylamine (i.e. the acid-cleavable Knorr carboxamide linker) or N-Fmoc-Thr(tBu)-OH (for non-cleavable experiments). The ratio of Fmoc-protected amino groups to DMT-protected hydroxyl residues on the beads was determined spectrophotometrically to be approximately 20:1. The beads were subjected to 20 cycles of oligonucleotide synthesis on an automated synthesizer using 3'-O-methyl-N,N-diisopropyl phosphoramidites of the following nucleosides: $N^6$-Bz-5'-O-DMT-(7-deaza)-2'-deoxyadenosine (Berry and Associates, Ann Arbor, Mich.), $N^4$-Bz-5'-O-DMT-2'-deoxycytidine, and 5'-O-DMT-thymidine (Glen Research).

The beads were then removed from the instrument and treated for 5 min. with 10% piperidine in DMF to remove the Fmoc protecting group. After coupling the first amino acid residue (N-Fmoc-Thr($^t$Bu)-OH), the beads were treated with a DMF solution of acetic anhydride and 1-methylimidazole to cap any unreacted amines. All peptide coupling reactions were run for 20 min. and contained 0.11M Fmoc-amino acid, 0.1M HBTU, 0.1M HOBt, and 0.3M DIEA in DMF. The beads were then subjected to two cycles of nucleotide addition on the synthesizer (detritylation with TCA; tetrazole-catalyzed phosphitylation; capping with acetic anhydride; oxidation with iodine in acetonitrile/water). Sequential steps of amino acid coupling and dinucleotide addition were repeated until synthesis of the peptide sequence RQFKVVT (SEQ ID NO:2) and construction of the oligonucleotide coding region had been completed. After performing an additional 35 cycles of oligonucleotide synthesis, the beads were treated sequentially with piperidine/DMF (1:9 for 8 min), thiophenol/triethylamine/dioxane (1:2:2 for 4 hr), ethylenediamine/ethanol (1:1 for 5 hr at 55° C.), and TFA/water (20:1 for 1 hr) to deprotect fully both the peptide and oligonucleotide chains. In experiments using the acid-cleavable linker, the supernatant from the TFA deprotection reaction was concentrated in vacuo, and the isolated crude peptide was then analyzed by HPLC.

C. Construction of an Encoded Library

The parallel synthesis chemistry outlined above was used in the construction of the library. The sites of peptide synthesis were differentiated from DNA synthesis sites in this experiment by coupling to all the beads a mixture of N-Fmoc-Thr($^t$Bu)-OBt and succinimidyl 4-O-DMT-oxybutyrate as described above. Sequences of oligonucleotide tags in the library deviated from ST08 only within the coding region. The 3'-conserved region of the oligonucleotide ST08 was first synthesized on a total bead mass of 35 mg (~$1.75 \times 10^8$ beads). The Fmoc protecting group was removed and the bead mass was divided into seven equal parts. To each aliquot was coupled one of seven different alpha-N-Fmoc-protected amino acids (side chain protecting groups are shown in parenthesis): Arg($N^G$-Pmc), Gln(Trt), Phe, Lys($^t$Boc), Val, D-Val and Thr($^t$Bu). Each part was then subjected to two rounds of automated oligonucleotide synthesis. The respective sequences of the appended dinucleotides that specified uniquely each different amino acid residue were TA, TC, CT, AT, TT, CA and AC. The beads were then pooled, mixed thoroughly, and the entire bead mass subjected to Fmoc deprotection.

This cycle of bead partitioning, peptide coupling, oligo-nucleotide dimer synthesis, bead recombination and Fmoc removal was repeated for a total of seven times. The final Fmoc protecting group was not removed. Rather, the pooled bead mass was subjected to 35 cycles of oligonucleotide synthesis. The library was then fully deprotected as described above.

D. Library Staining and FACS Analysis

A portion of a library (typically 0.5–2 mg of beads) was suspended in blocking buffer (PBS, 1% BSA, 0.05% Tween-20) and incubated at room temperature for 1 hr. The beads were pelleted by centrifugation and resuspended in a solution of mAb D32.39 (10 mg/mL in blocking buffer). The suspension was incubated on ice for 30 min., pelleted by centrifugation, and washed with blocking buffer. The beads were then suspended in a solution of phycoerythrin-conjugated goat anti-mouse antibody (Molecular Probes) for 20 min. on ice. The beads were washed in blocking buffer and diluted in PBS for delivery into the fluorescence activated cell sorting (FACS) instrument (Becton Dickinson FACStar Plus). Beads which had bound the mAb D32.39 were identified by their acquired fluorescence. Individual beads from both the most brightly stained 0.17% of the library and from the region having the lowest fluorescence (ca. 98%) were sorted into PCR microfuge vials. Specific binding of D32.39 to the beads was blocked by preincubation of the mAb with the soluble peptide Ac-RQFKVVT-OH (SEQ ID NO:2) at a final concentration of 10 µM.

E. PCR of Bead-Bound Template

PCR amplifications were performed in the manufacturer supplied buffer system (50 mM KCl, 10 mM Tris-HCl, pH 9.0, 0.1% Triton X-100, 2 mM $MgCl_2$) with 0.2 mM dATP, dCTP, and dGTP, 0.8 mM dUTP, 2 mM each primer, 3 units Taq polymerase (Promega), and 1 unit of uracil DNA glycosylase (Gibco BRL) (total volume 70 µL). The primer sequences, 5'-ATC CAA TCT CTC CAC-3' (SP13) (SEQ ID NO:2) and 5'-(biotin)-GTG GAA TGG AAG TGA-3' (SP14) (SEQ ID NO:22) were respectively homologous and complementary to the template ST08. PCR reactions consisted of 45 cycles of denaturation at 95° C. for 30 sec., primer annealing at 50° C. for 1 min., and extension at 72° C. for 1 min. Reactions were analyzed by electrophoresis in 20% acrylamide or 2% low melting point agarose gels.

F. Sequencing of PCR Product

Biotinylated PCR product from individual reactions was isolated with streptavidin-coated magnetic beads (Dynal, Inc.). After alkaline elution of the non-biotinylated strand and washing, each bead sample was treated with sequencing cocktail. Dideoxy sequencing was performed using the primer 5'-ATC TCT ATA CTA TCA-3' (SP15) (SEQ ID NO:23) and Bst polymerase (Bio-Rad) according to the manufacturer's instructions, with the exception that a 1:100 ratio of deoxy- to dideoxynucleotide triphosphates (Pharmacia) was employed.

G. Determination of Peptide Binding Affinities

The binding affinities of various peptides for the monoclonal antibody D32.39 were measured in a competition binding experiment. A tracer peptide (LRRASLGGGRRQFKVVT (SEQ ID NO:24); 50 pM) containing the known epitope for D32.39 fused to a consensus substrate sequence for cAMP-dependent protein kinase was radiolabelled to high specific activity with [g $-^{33}$P]ATP (see Liet al., 1989, Proc. Natl. Acad. Sci. USA 86: 558–562, incorporated herein by reference) and mixed with various concentrations of the peptide of interest (10 µM–1 pM). The peptide mixtures were added to polystyrene wells coated with D32.39 (0.1 µg/mL). Samples were incubated 2 hr. at 4° C., the wells washed with PBS, and the radioactivity associated with each well was counted and used to generate a competitive binding curve. Under the conditions of the assay the $IC_{50}$ should be close to the dissociation constant (Kd) for the peptide.

We claim:

1. A method of screening a tagged library of diverse compounds, wherein said library comprises a plurality of different members, each member comprising:

a solid support;

multiple copies of a compound bound to each of said supports, wherein the compound bound to one of said supports is different from the compound bound to selected other solid supports, and wherein said compound comprises a peptide; and one or more identifier tags bound to each of said solid supports, wherein said tag identifies the compound bound to said solid support or identifies a reaction said solid support has experienced, and wherein said tag is an oligonucleotide or a fluorescent tag, said method comprising the steps of:

a) cleaving at least a portion of said compounds from said solid supports to yield a collection of untagged soluble compounds wherein said tags remain bound to said solid supports;

b) incubating said collection of untagged soluble compound s with a receptor under conditions conducive to binding of a ligand to said receptor; and c) c) determining whether any compounds of said collection have bound to the receptor.

2. The method of claim 1 wherein said solid support is a bead 50 to 500 microns in diameter.

3. The method of claim 1, wherein said identifier tag is covalently attached to a first linker and said first linker is attached to said solid support and not to said compound.

4. The method of claim 1, whrein all of said compounds on said solid supports are cleaved prior to said incubation step.

5. The method of claim 1, further comprising the step of deducing the structure of the compounds that have bound to the receptor by examining the tags associated with the receptor-bound compounds.

6. The method of claim 1, wherein said receptor is a mixture of receptors and wherein each receptor bears a receptor-identifier tag that identifies the receptor.

7. The method of claim 1, wherein said receptor is immobilized on a second solid support.

8. The method of claim 7, wherein said second solid support is a surface or portion of the surface of a small individual compartment or well.

9. The method of claim 1, wherein said compound is attached to said solid support by a cleavable linker.

10. The method of claim 9, wherein said cleavable linker is a mixture of cleavable linkers.

11. The method of claim 10, wherein only a portion of said compounds on said solid supports are cleaved prior to said incubation step.

12. In a method of synthesizing a synthetic peptide library comprising a plurality of different members, each member comprising a peptide composed of a sequence of amino acid monomers linked to a bead to which bead is also linked one or more oligonucleotide identifier tags identifying the sequence of monomers in said peptide, wherein said amino acid monomers are protected with Fmoc and piperidine is used to remove the Fmoc protecting group, the improvement comprising effecting Fmoc removal by treatment with 5 to 15% piperidine for 5 to 60 minutes or 15 to 30% piperidine for 1 to 30 minutes.

13. The improvement of claim 12, wherein said bead is about 10 μm in diameter and composed of a macroporous styrene-divinylbenzene copolymer derivatized with a dodecylamine linker.

14. The improvement of claim 12, wherein said amino acid monomers have side $^t$Bu side chain protecting groups, trifluoroacetic acid is used to remove said $^t$Bu side chain protecting groups, and said oligonucleotide tags comprise 7-deaza-2'-deoxyadenosine.

* * * * *